US007141688B2

(12) United States Patent
Feng et al.

(10) Patent No.: US 7,141,688 B2
(45) Date of Patent: Nov. 28, 2006

(54) FLUORINATED DYE STABILIZERS IN FLUORINATED DIELECTRIC SOLVENT

(75) Inventors: Kai-Chia Feng, San Mateo, CA (US); Ying-Syi Li, San Jose, CA (US); Jin Yang, San Jose, CA (US); HongMei Zang, Sunnyvale, CA (US); Haiyan Gu, Davis, CA (US); Sundaravel P. Ananthavel, Alameda, CA (US); Rong-Chang Liang, Cupertino, CA (US)

(73) Assignee: SiPix Imaging, Inc., Freemont, CA (US)

( * ) Notice: Subject to any disclaimer, the term of this patent is extended or adjusted under 35 U.S.C. 154(b) by 555 days.

(21) Appl. No.: 10/686,501

(22) Filed: Oct. 14, 2003

(65) Prior Publication Data

US 2004/0131958 A1 Jul. 8, 2004

Related U.S. Application Data

(60) Provisional application No. 60/436,907, filed on Dec. 24, 2002, provisional application No. 60/418,847, filed on Oct. 15, 2002.

(51) Int. Cl.
- C07F 19/00 (2006.01)
- C09B 62/00 (2006.01)
- C02B 26/00 (2006.01)
- C07C 49/00 (2006.01)

(52) U.S. Cl. .......................... 556/32; 556/45; 556/51; 556/53; 556/113; 556/117; 556/135; 556/136; 556/137; 556/150; 540/126; 568/333; 548/257; 544/180; 359/296

(58) Field of Classification Search ................ 568/333; 548/257; 544/180; 556/32, 45, 51, 53, 113, 556/117, 135, 136, 137, 150; 359/296; 540/126
See application file for complete search history.

(56) References Cited

U.S. PATENT DOCUMENTS

| 3,281,426 A | 10/1966 | Tiers ...................... 260/314.5 |
| 4,241,154 A | 12/1980 | Hara et al. .................... 430/17 |
| 4,246,330 A | 1/1981 | Hara et al. .................... 430/17 |
| 4,544,372 A | 10/1985 | Heise et al. .................. 264/2.1 |
| 4,775,386 A | 10/1988 | Reinert et al. ................. 8/442 |
| 5,930,026 A | 7/1999 | Jacobson et al. ........... 359/296 |
| 5,961,804 A | 10/1999 | Jacobson et al. ........... 204/606 |

FOREIGN PATENT DOCUMENTS

| DE | 2327987 | 1/1975 |
| GB | 2 027 731 | 2/1980 |
| JP | 59-083162 | 5/1984 |
| JP | 62-233293 | 10/1987 |
| WO | PCT/US03/32777 | 5/2004 |

OTHER PUBLICATIONS

U.S. Appl. No. 09/518,488, filed Mar. 2000.
U.S. Appl. No. 09/606,654, filed Jun. 2000.
U.S. Appl. No. 09/784,972, filed Feb. 2001.
U.S. Appl. No. 10/335,051, filed Dec. 2002.
U.S. Appl. No. 10/335,210, filed Dec. 2002.
U.S. Appl. No. 10/439,428, filed May 2003.
U.S. Appl. No. 10/632,171, filed Jul. 2003.
Allen, K. (Oct. 2003). Electrophoretics Fulfilled. *Emerging Displays Review: Emerging Display Technologies, Monthly Report* Oct. 9-14, 2003.
Chen, S.M. (Jul. 2003) The Application for the Revolutionary Electronic Paper Technology, *OPTO News & Letters*, 102, 37-41. (in Chinese, English abstract attached, full translation available upon request).
Chen, S.M. (May 2003) The New Applications and the Dynamics of Companies. *TRI.* 1-10. (In Chinese, English abstract attached, full translation availabe upon request).
Balch, A.L., Dance, I.G. & Holm, R.H. (1968) "The Characterization of Dimeric Dithiolene Complexes", *Journal of the American Chemical Society*, vol. 90, No. 5, 1139-1145.
Brown, A.S. & MacInnes, D.A. (Mar. 1935). The Determination of the Solubility of Silver Chloride by an Electrometric Titration Method. *J. Amer.Chemical Society*, vol. 57, 459-465.
Hopper, M.A. & Novotny, V., (1979). An Electrophoretic Display, Its Properties, Model, and Addressing. *IEEE Trans. Electr. Dev.*, vol. ED-26, No. 8, 1148-1152.
Lee, H., & Liang, R.C. (Jun. 2003) SiPix Microcup(R) Electronic Paper—An Introduction. *Advanced Display*, 3, 4-9 (in Chinese, English abstract attached, full translation available upon request).
Liang, R.C. (Feb. 2003) *Microcup(R) Electrophoretic and Liquid Crystal Displays by Roll-to-Roll Manufacturing Processes*, Presentation conducted at the Flexible Microelectronics & Displays Conference of U.S. Display Consortium, Phoenix, Arizona, USA.
Liang, R.C., Hou, J., Chung, J., Wang, X., Pereira, C., & Chen, Y. (2003). Microcup(R) Active and Passive Matrix Electrophoretic Displays by A Roll-to-Roll Manufacturing Processes. *SID Digest*, 20.1.
Liang, R.C., Hou, J., Zang, H.M., Chung, J., & Tseng, S. (2003) Microcup(R) displays : Electronic Paper by Roll-to-Roll Manufacturing Processes. *Journal of the SID*, 11(4), 621-628.

(Continued)

*Primary Examiner*—Porfirio Nazario-Gonzalez
(74) *Attorney, Agent, or Firm*—Howrey LLP

(57) ABSTRACT

The present invention is directed to novel fluorinated dye stabilizers having both high quenching efficiency and solubility in halogenated solvents. These dye stabilizers have shown a significantly effect on improving the dye fastness in hostile photooxidation conditions.

62 Claims, No Drawings

OTHER PUBLICATIONS

Liang, R.C., Hou, J., Zang, H.M., & Chung, J. (Feb. 2003). *Passive Matrix Microcup(R) Electrophoretic Displays*. Paper presented at the IDMC, Taipei, Taiwan.

Liang, R.C., Hou, J., & Zang, H.M. (Dec. 2002) Microcup Electrophoretic Displays by Roll-to-Roll Manufacturing Processes, *IDW*, EP2-2, 1337-1340.

Liang, R.C., & Tseng, S. (Feb. 2003). *Microcup(R) LCD, An New Type of Dispersed LCD by A Roll-to-Roll Manufacturing Process*. Paper presented at the IDMC, Taipei, Taiwan.

Miyaura, N., Ishiyama, T., Sasaki, H., Ishikawa, M., Satoh, M. & Suzuki, A.(1989). Palladium-Catalyzed Inter- and Intramolecular Cross-Coupling Reactions of B-Alkyl-9-borabicyclo[3.3.1]nonane Derivatives with 1-Halo-1-alkenes or Haloarenes. Syntheses of Functionalized Alkenes, Arenes, and Chcloalkenes via a Hydroboration-Coupling Sequence, *J. Am. Chem. Soc.*, vol. 111, 314-321.

Monroe, B.M. & Mrowca, J.J. (1979). Quenching of Singlet Oxygen by Nickel Complexes, *The Journal of Physical Chemistry*, vol. 83, No. 5, 591-595.

Nikkei Microdevices. (Dec. 2002) Newly-Developed Color Electronic Paper Promises—Unbeatable Production Efficiency. *Nikkei Microdevices*, , 3. (in Japanese, with English translation).

Int'l Search Report Wing, R.M., Tustin, G.C. & Okamura, W.H. (Apr. 1970) "The Oxidative Cycloaddition of Metal Dithiolenes to Olefins. Synthesis and Characterization of Norbornadiene-Bis-*cis*(1,2-perfluoromethylene-1, 2-dithiolato)nickel", Journal of the American Chemical Society, vol. 92, 1935-1939.

Zang, H.M., & Liang, R.C. (2003) Microcup Electronic Paper by Roll-to-Roll Manufacturing Processes. *The Spectrum*, 16(2), 16-21.

FLUORINATED DYE STABILIZERS IN FLUORINATED DIELECTRIC SOLVENT

RELATED APPLICATIONS

This application claims the priority under 35 USC 119(e) of U.S. Provisional Applications No. 60/418,847, filed Oct. 15, 2002, and 60/436,907, filed Dec. 24, 2002. The whole content of each of these applications is incorporated into this application by reference.

BACKGROUND OF THE INVENTION

1. Field of the Invention

This invention relates to a group of compounds which are useful for stabilizing the dyes in an electrophoretic display system.

2. Brief Description of Related Art

The electrophoretic display (EPD) is a non-emissive device based on the electrophoresis phenomenon influencing the migration of charged pigment particles in a solvent, preferably a colored dielectric solvent. This type of display was first proposed in 1969. An EPD typically comprises a pair of opposed and spaced-apart plate-like electrodes, with spacers predetermining a certain distance between the electrodes. At least one of the electrodes, typically on the viewing side, is transparent. For the passive type of EPDs, row and column electrodes on the top (the viewing side) and bottom plates respectively, are needed to drive the displays. In contrast, an array of thin film transistors (TFTs) on the bottom plate and a common, non-patterned transparent conductor plate on the top viewing substrate are required for the active type EPDs.

An electrophoretic fluid composed of a colored dielectric solvent or solvent mixture and charged pigment particles dispersed therein is enclosed between the two electrode plates. When a voltage difference is imposed between the two electrode plates, the pigment particles migrate by attraction to the plate of polarity opposite that of the pigment particles. Thus, the color showing at the transparent plate, determined by selectively charging the plates, can be either the color of the solvent or the color of the pigment particles. Reversal of plate polarity will cause the particles to migrate back to the opposite plate, thereby reversing the color. Intermediate color density (or shades of gray) due to intermediate pigment density at the transparent plate may be obtained by controlling the plate charge through a range of voltages or pulsing time.

EPDs of different pixel or cell structures have been reported previously, for example, the partition-type EPD (M. A. Hopper and V. Novotny, IEEE Trans. Electr. Dev., Vol. ED 26, No. 8, pp. 1148–1152 (1979)) and the microencapsulated EPD (U.S. Pat. Nos. 5,961,804 and 5,930,026).

An improved EPD technology was disclosed in co-pending applications, U.S. Ser. No. 09/518,488 filed on Mar. 3, 2000 (corresponding to WO 01/67170), U.S. Ser. No. 09/606,654 filed on Jun. 28, 2000 (corresponding to WO 02/01281) and U.S. Ser. No. 09/784,972 filed on Feb. 15, 2001 (corresponding to WO02/65215), all of which are incorporated herein by reference. The improved EPD comprises isolated cells formed from microcups and filled with charged particles dispersed in a dielectric solvent. The filled cells are individually sealed with a polymeric sealing layer, preferably formed from a composition comprising a material selected from a group consisting of thermoplastics, thermosets and precursors thereof.

For any type of the electrophoretic displays, the electrophoretic fluid contained within the display cells is undoubtedly one of the most crucial parts of the device. The fluid, as stated earlier, usually is composed of pigment particles dispersed in a dielectric solvent or solvent mixture. Halogenated solvents of a high specific gravity have been widely used as the dielectric solvent in EPD applications, particularly those involving an inorganic pigment, such as $TiO_2$, as the charged particles. The halogenated solvents of a high specific gravity are very useful in reducing the rate of sedimentation of the pigment particles in the solvent. Fluorinated solvents are among the most preferred because they are chemically stable and environmentally friendly.

The display fluid may be colored by dissolving or dispersing a dye or colorant in the dielectric solvent or solvent mixture. However, the color of the dye or colorant may fade due to thermal and/or photooxidation. To remedy this problem, a stabilizer or quencher is often added to the fluid to inhibit or suppress photooxidation of the dye or colorant through quenching the excited state and in some cases, quenching the radicals present in the system. Radical quenchers or inhibitors include phenols, oximes, TEMPO, nitroso compounds or derivatives and metal complexes thereof. Metal complexes are of particular interest because of their high efficiency in quenching the excited state and inhibiting the photooxidation process. Unfortunately, most quenchers are not soluble in halogenated dielectric solvents, particularly not in fluorinated solvents.

SUMMARY OF THE INVENTION

The present invention is directed to a group of novel fluorinated dye stabilizers having both high quenching efficiency and solubility in halogenated solvents. These dye stabilizers have shown a significant effect on improving the dye fastness in hostile thermal and/or photooxidation conditions.

The first aspect of the invention is directed to a group of novel dye stabilizers.

The second aspect of the invention relates to an electrophoretic fluid which comprises charged pigment particles dispersed in a halogenated dielectric solvent or solvent mixture, a dye and a dye stabilizer of the present invention.

The third aspect of the invention is directed to an electrophoretic display the cells of which are filled with an electrophoretic fluid comprising charged pigment particles dispersed in a halogenated dielectric solvent or solvent mixture, a dye and a dye stabilizer of the present invention.

DETAILED DESCRIPTION OF THE INVENTION

I. Definitions

Unless defined otherwise in this specification, all technical terms are used herein according to their conventional definitions as they are commonly used and understood by those of ordinary skill in the art.

The term "alkyl" refers to a linear or branched hydrocarbon chain and its unsaturated derivatives. Unless specifically indicated, the alkyl chain, in the context of the present application, has 1 to 30 carbon atoms, preferably 1 to 18 carbon atoms, such as methyl, ethyl, octyl, n-decyl or the like.

The term "cycloalkyl" refers to a cyclic hydrocarbon moiety of 3 to 30 carbon atoms, preferably 3 to 18 carbon atoms, such as cyclopropyl, cyclohexyl, cyclododecyl or the like.

The term "alkylene" refers to an alkyl moiety which may be substituted at both ends. In the context of the present application, an alkylene may have 1 to 30 carbon atoms, preferably 1 to 18 carbon atoms, more preferably 1 to 8 carbon atoms.

The term "heteroalkyl" refers to an "alkyl" as defined above in which one or more carbon atoms are replaced by O, S or N.

The term "alkoxy" refers to the group —OR wherein R is an alkyl or cycloalkyl as defined above.

The term "aryl", as in "aryl" or "aryloxy", refers to an organic radical derived from an aromatic ring having 6 to 18 carbon atoms, such as phenyl, naphthyl, anthracenyl or the like.

The term "aryloxy" refers to the group —OR wherein R is an aryl as defined above.

The term "heteroaryl" refers to an organic radical derived from an aromatic hydrocarbon in which one or more of the ring carbon atoms are replaced by O, S or N, such as pyridyl, thienyl, furanyl, pyrrolyl or the like.

The term "heterocyclic" or "heterocyclyl" refers to a saturated or unsaturated cyclic hydrocarbon moiety of 4 to 30 carbon atoms wherein the hydrocarbon moiety further comprises one or more heteroatoms such as O, S or N.

When referring to "carbonyl" in this application, it is intended to cover optionally substituted carbonyl which may be expressed as, but is not limited to, R—C(=O)— wherein R is hydrogen, alkyl, aryl, heteroalkyl or heteroaryl.

When referring to "sulfonyl" in this application, it is intended to cover optionally substituted sulfonyl which may be expressed as, but is not limited to, R—S(O$_2$)— wherein R is hydrogen, alkyl, aryl, heteroalkyl or heteroaryl.

When referring to "amido" in this application, it is intended to cover optionally substituted amido which may be expressed as, but is not limited to, R—C(O)NH— or R—NHC(O)— wherein R is hydrogen, alkyl, aryl, heteroalkyl or heteroaryl.

When referring to "sulfonamido" in this application, it is intended to cover optionally substituted sulfonamide which may be expressed as, but is not limited to, R—NHS(O$_2$)— or R—S(O$_2$)NH— wherein R is hydrogen, alkyl, aryl, heteroalkyl or heteroaryl.

The term "halogenated" or "fluorinated" refers to a moiety which is partially or completely substituted with halogen atoms or fluorine atoms, respectively. For example, the term "fluoroalkyl" or "fluorinated alkyl" refers to an alkyl in which some or all of the hydrogen atoms in the alkyl moiety are replaced with fluorine atoms.

The "alkyl" or "aryl" group, in the context of the present application, may be optionally substituted with one or more of the following: alkyl, aryl, alkylaryl, arylalkyl, —NCO, —NO$_2$, NC—, HO(O)C—, R*O—, R*$_2$N—, R*S—, R*CO—, R*C(O)O—, R*O(O)C—, R*NHC(O)—, R*$_2$NC(O)—, R*NHC(O)O—, R*OC(O)NH—, R*C(O)NH—, R*C(S)NH—, R*NHC(O)NH—, R*NHC(S)NH—, R*SC(O)NH—, R*=N—, R*NHC(O)S— and the like wherein R* is hydrogen, an alkyl, aryl, alkylaryl or arylalkyl. Preferably, "alkyl" and "aryl" are unsubstituted or substituted with an alkyl or aryl, more preferably, unsubstituted.

Naming of complex substituents follows the rule that the secondary substituent on the moiety being substituted is named first and the primary substituent through which the secondary substituent is connected to the moiety being substituted is named second. Thus an "arylalkyl" radical is an alkyl radical (as defined) that is substituted by an aryl radical (as defined), etc.

I. Novel Dye Stabilizers

The dye stabilizers can be represented by Formula 1 below:

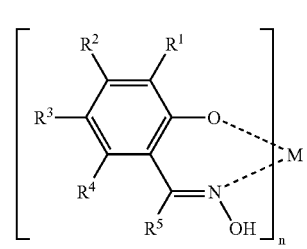

Formula 1 wherein:

M is a metal ion, preferably Ni, Co, Cu, Fe, Mn, Zr, Pd, Pt, Mg, Al or Zn;

n is 2 or 3;

$R^1$, $R^2$, $R^3$, $R^4$ and $R^5$ are, independently, $R_f$-A- (wherein $R_f$ and A are defined below), hydrogen, hydroxyl, halogen, nitro, cyano, alkyl, heteroalkyl, aryl, heteroaryl, alkylaryl, arylalkyl, alkyl-heteroaryl, heteroalkylaryl, aryl-heteroalkyl, heteroarylalkyl, alkoxy, aryloxy, benzoyl, acetyl, carbonyl, sulfonyl, amido, carbamoyl, sulfonamido, sulfamoyl or heterocyclyl, or any two of $R^1$, $R^2$, $R^3$, $R^4$ or $R^5$ together may form a cycloalkyl or heterocyclic group, provided that at least one of $R^1$, $R^2$, $R^3$, $R^4$ and $R^5$ is $R_f$-A-;

A in $R_f$-A- is absent, oxygen or an alkylene chain; and $R_f$ is a fluorinated alkyl or aryl or a low/medium molecular weight fluorinated polymeric or oligomeric moiety.

Dye stabilizers represented by Formula 2 and 3 below are also useful:

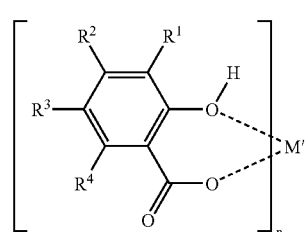

Formula 2

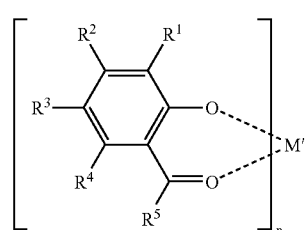

Formula 3 wherein:

M' is absent or a metal ion, preferably Ni, Co, Cu, Fe, Mn, Zr, Pd, Pt, Mg, Al or Zn;

n is 2 or 3;

$R^1$, $R^2$, $R^3$, $R^4$ and $R^5$ are independently, $R_f$-A- (wherein $R_f$ and A are defined below), hydrogen, hydroxyl, halogen, nitro, cyano, alkyl, heteroalkyl, aryl, heteroaryl, alkylaryl, arylalkyl, alkyl-heteroaryl, heteroalkylaryl, aryl-heteroalkyl, heteroarylalkyl, alkoxy, aryloxy, benzoyl, acetyl, carbonyl, sulfonyl, amido, carbamoyl, sulfonamido, sulfamoyl or heterocyclyl, or any two of $R^1$, $R^2$, $R^3$ or $R^4$ in Formula 2 or any two of $R^1$, $R^2$, $R^3$, $R^4$ or $R^5$ in Formula 3 together may form a cycloalkyl or heterocyclic group, provided that at least one of $R^1$, $R^2$, $R^3$ and $R^4$ in Formula 2 and at least one of $R^1$, $R^2$, $R^3$, $R^4$ and $R^5$ in Formula 3 is $R_f$-A-;

A in $R_f$-A- is absent, oxygen or an alkylene chain; and $R_f$ is a fluorinated alkyl or aryl or a low/medium molecular weight fluorinated polymeric or oligomeric moiety.

Dye stabilizers represented by Formula 4, Formula 5 and Formula 6 are also useful:

Formula 4

Formula 5

Formula 6 wherein:

$R^1$, $R^2$ and $R^3$ are independently, $R_f$-A- (wherein $R_f$ and A are defined below), hydrogen, hydroxyl, halogen, nitro, cyano, alkyl, heteroalkyl, aryl, heteroaryl, alkylaryl, arylalkyl, alkyl-heteroaryl, heteroalkylaryl, aryl-heteroalkyl, heteroarylalkyl, alkoxy, aryloxy, benzoyl, acetyl, carbonyl, sulfonyl, amido, carbamoyl, sulfonamido, sulfamoyl or heterocyclyl, provided at least one of $R^1$ and $R^2$ in Formula 4 or 5 and at least one of $R^1$, $R^2$ and $R^3$ in Formula 6 is $R_f$-A-;

A in $R_f$-A- is absent, oxygen or an alkylene chain; and $R_f$ is a fluorinated alkyl or aryl or a low/medium molecular weight fluorinated polymeric or oligomeric moiety.

While not explicitly expressed, it is understood that the present invention also encompasses compounds of Formula 4 in which there are more than one $R^1$ and/or more than one $R^2$ on each of the phenyl moiety; compounds of Formula 5 in which there are more than one $R^1$ and/or more than one $R^2$ on each of the phenyl moiety; and compounds of Formula 6 in which there are more than one $R^3$ on the phenyl moiety. In such cases, the multiple $R^1$s, $R^2$s or $R^3$s may be the same or different.

Dye stabilizers represented by Formula 7 are also useful:

Formula 7 wherein:

M is a metal ion, preferably Ni, Co, Cu, Fe, Mn, Zr, Pd, Pt, Mg, Al or Zn;

n is 2 or 3

$R^1$ and $R^2$ are independently, $R_f$-A- (wherein $R_f$ and A are defined below), hydrogen, hydroxyl, halogen, nitro, cyano, alkyl, heteroalkyl, aryl, heteroaryl, alkylaryl, arylalkyl, alkyl-heteroaryl, heteroalkylaryl, aryl-heteroalkyl, heteroarylalkyl, alkoxy, aryloxy, benzoyl, acetyl, carbonyl, sulfonyl, amido, carbamoyl, sulfonamido, sulfamoyl or heterocyclyl, provided at least one of $R^1$ and $R^2$ is $R_f$-A-;

A in $R_f$-A- is absent, oxygen or an alkylene chain; and $R_f$ is a fluorinated alkyl or aryl or a low/medium molecular weight fluorinated polymeric or oligomeric moiety.

In one embodiment, the metal ion may be a divalent metal ion.

In one embodiment, $R^1$, $R^2$, $R^3$, $R^4$ and $R^5$ in Formula 1 or 3, $R^1$, $R^2$, $R^3$ and $R^4$ in Formula 2, $R^1$ and $R^2$ in Formula 4, 5 or 7 and $R^1$, $R^2$ and $R^3$ in Formula 6, are independently hydrogen, hydroxyl, alkyl, heteroalkyl, alkoxy, acetyl or amido. In another embodiment, $R^1$, $R^2$, $R^3$, $R^4$ and $R^5$ in Formula 1 or 3, $R^1$, $R^2$, $R^3$ and $R^4$ in Formula 2, $R^1$ and $R^2$ in Formula 4, 5 or 7 and $R^1$, $R^2$ and $R^3$ in Formula 6, are independently hydrogen, hydroxyl, alkyl or alkoxy.

In one embodiment of Formula 1 or 3, one of $R^1$, $R^2$, $R^3$, $R^4$ and $R^5$ may be $R_f$-A- and the remaining four may be independently hydrogen or alkyl. In another embodiment of Formula 1 or 3, one of $R^1$, $R^2$, $R^3$ and $R^4$ is $R_f$-A-, $R^5$ may be alkyl and the remaining three may be all hydrogen.

In one embodiment of Formula 2, one of $R^1$, $R^2$, $R^3$ and $R^4$ may be $R_f$-A- and the remaining three may be independently hydrogen or alkyl.

In one embodiment of Formula 4, 5 or 7, one of $R^1$ and $R^2$ may be $R_f$-A- and the other may be hydrogen or alkyl.

In one embodiment of Formula 6, one of $R^1$, $R^2$ and $R^3$ may be $R_f$-A- and the other two may be independently hydrogen or alkyl.

In another embodiment, $R_f$ may be a completely or partially fluorinated alkyl of 6 to 20 carbon atoms.

In yet a further embodiment, $R_f$ may be a low/medium molecular weight fluorinated polymeric or oligomeric moiety prepared from one or more types of fluorinated monomer such as epoxide, hydrofuran, cyclolactone, cyclolactam, acrylate, methacrylate or vinyl (including styrene, vinylether, vinylalkane and the like).

When $R_f$ is fluorinated polymeric or oligomeric moiety, its molecular weight preferably is about 100 to about 100,000, more preferably about 200 to about 20,000 and most preferably about 400 to about 10,000. Examples of $R_f$ may include, but are not limited to, fluoropolyether and hydrofluoropolyether derived from the monomer, fluoropropylene oxide, or from the oligomer such as Krytox® K-fluids (trifluorohomopolymer) from Dupont and HT or ZT series from Solvay Solexis; and poly(chlorotrifluoroethylene) derived from the monomer, chlorotrifluoroethylene, or from the oligomer such as Halocarbon Oils from Halocarbon Product Corp. (River Edge, N.J.).

$R_f$ may also be prepared by copolymerization of fluorinated monomer(s) with non-fluorinated monomer(s).

In one embodiment, $R_f$ is a monovalent radical derived from a halogenated, especially a fluorinated, optionally substituted alkylene or alkylene oxide homopolymer or copolymer.

In another embodiment, $R_f$ is a polymeric chain derived from a fluorinated epoxide.

In another embodiment, $R_f$ is represented by Formula (A) below:

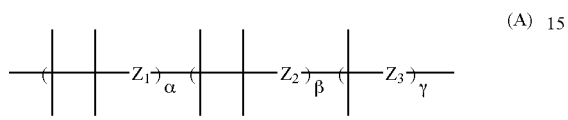
(A)

wherein the open substituent positions (not designated) on the main chain of $R_f$ can be the same or different and may independently be selected from a group consisting of hydrogen, halogen (especially fluoro), alkyl, aryl, alkylaryl, fluoroalkyl, fluoroaryl, fluoroalkylaryl, $-OR^{11}$, $OCOR^{11}$, $-COOR^{11}$, $-CONR^{11}R^{12}$ (wherein $R^{11}$ and $R^{12}$ are independently hydrogen, alkyl, aryl, alkylaryl, fluoroalkyl, fluoroaryl, fluoroalkylaryl or fluorinated polyether) and substituted derivatives thereof;

$Z_1$, $Z_2$ and $Z_3$ are independently oxygen or absent;

$\alpha$, $\beta$ and $\gamma$ are the weight fractions of the corresponding repeating units and are independently in the range of 0–1 with their sum no greater than 1.

The open substituent positions preferably are independently hydrogen, fluorine and a fluorinated alkyl such as fluorinated methyl.

The alkyl group referred to in Formula (A) may have 1–20 carbon atoms and the aryl group may have 6–18 carbon atoms.

In another embodiment, the substituents, $R^1$, $R^2$, $R^3$, $R^4$ and $R^5$ in Formula 1 or 3, $R^1$, $R^2$, $R^3$ and $R^4$ in Formula 2, $R^1$ and $R^2$ in Formula 4, 5 or 7 and $R^1$, $R^2$ and $R^3$ in Formula 6, are so selected that the total fluorine content of the dye stabilizer molecule is at least 10%, preferably at least 20% and more preferably at least 50%, by weight of the molecule.

II. Synthesis of Fluorinated Dye Stabilizers

The dye stabilizers of the present invention may be synthesized by methods known in the art. Eight possible reaction routes are illustrated in this section. However, it is understood that the reaction conditions may be readily modified and equivalent reagents substituted, all of which would be apparent to those skilled in the art.

II(A) Synthesis from 2,5-Hydroxyacetophenone

Reaction Scheme I

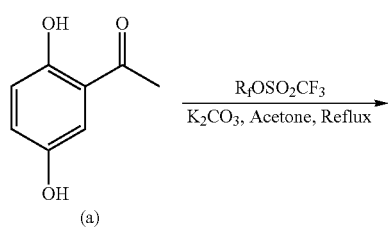

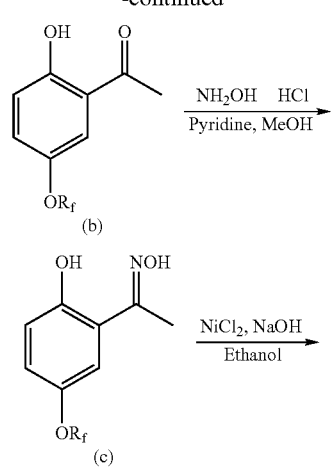

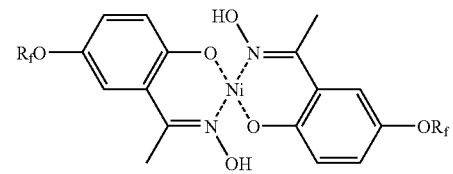

Formula 1

Reaction scheme I illustrates the general procedure for synthesis of a dye stabilizer of Formula 1 from 2,5-dihydroxyacetophenone (Compound a) which is commercially available from Aldrich. 2-Hydroxy-5-perfluoroalkoxy acetophenone (Compound b) is synthesized by refluxing 2,5-dihydroxyacetophenone with a fluorinating agent such as perfluorotriflate in a polar solvent. Suitable solvents include alkali acetone, dimethylformamide, tetrahydrofuran and the like. After the compound of Formula b is prepared, it may be converted into its oxime (Compound c) by methods known in the art for converting a ketone to its corresponding oxime, such as reacting the ketone with hydroxyl amine hydrochloride and pyridine in an alcoholic solvent, preferably methanol.

The dye stabilizer of Formula 1 is then synthesized by refluxing an ethanolic solution of the oxime ligand and a metal halide in a 2:1 ratio. Preferred metal halides include nickel chloride.

Reaction scheme I is particularly favorable for the synthesis of a dye stabilizer of the present invention in which at least one of $R^1$–$R^5$ is $R_f$A- wherein A is oxygen.

II(B) Synthesis from 2-Hydroxyacetophenone

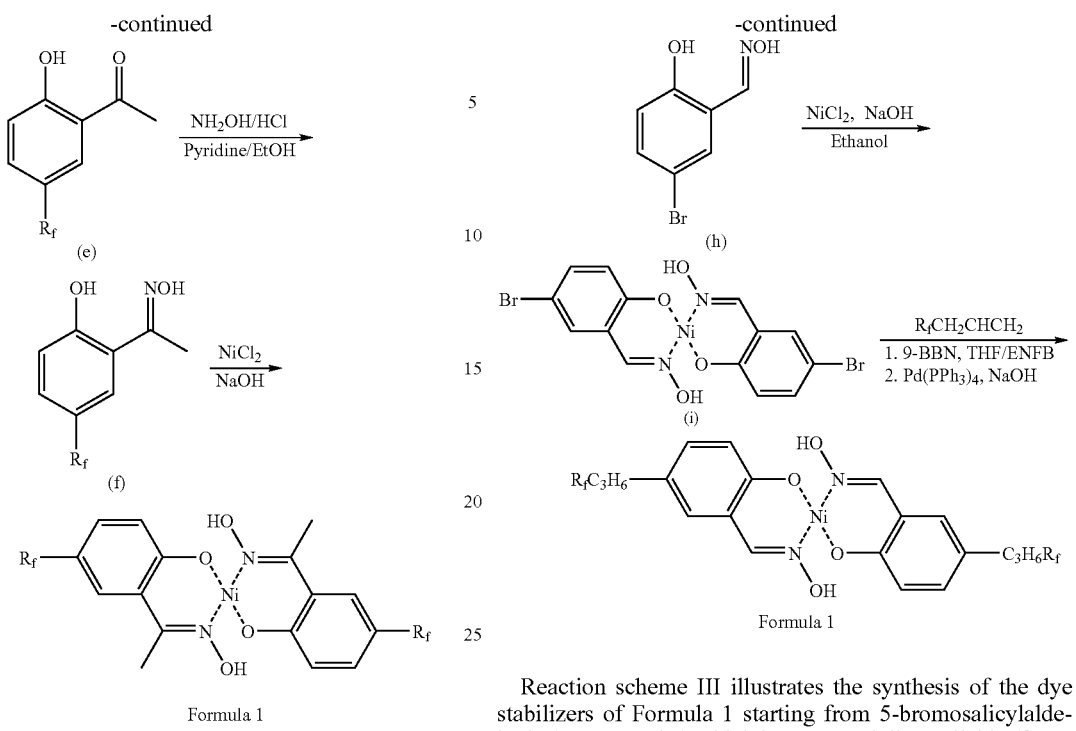

Formula 1

Alternatively, the dye stabilizers of Formula 1 may be prepared according to reaction scheme II starting from 2-hydroxyacetophenone (Compound d) which is also commercially available (from, for example, Aldrich). The 2-hydroxyacetophenone may be reacted with a fluorinating agent such as perfluoroalkyl iodide in the presence of a sulfinato-dehalogenation reagent (such as the $Na_2SO_4$—$NaHCO_3$ system) and aqueous NaOH to form Compound (e), 2-hydroxy-5-perfluoralkyl acetophenone. The reaction is preferably carried out at room temperature. The conversion of the ketone (Compound e) to its oxime (Compound f) and the subsequent synthesis of a dye stabilizer of Formula 1 are conducted in the same manner as the corresponding steps in reaction scheme I.

Reaction scheme II is particularly favorable for the synthesis of a dye stabilizer of the present invention in which one of $R^1$–$R^5$ is $R_f$-A- wherein A is absent.

II(C) Synthesis from 5-Bromosalicylaldehyde

Reaction Scheme III

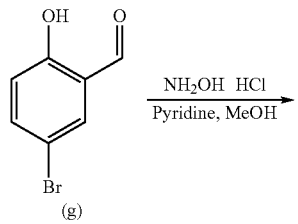

Reaction scheme III illustrates the synthesis of the dye stabilizers of Formula 1 starting from 5-bromosalicylaldehyde (Compound g) which is commercially available (from, for example, Aldrich). The oxime of Formula (h) may be prepared by methods known in the art for converting an aldehyde to the corresponding oxime, such as by reacting the aldehyde with hydroxylamine hydrochloride and pyridine in methanol. The metal chelate of Formula (i) may be synthesized by refluxing an ethanolic solution of the oxime of Formula (h) with a metal halide in a 2:1 ratio. The metal chelate of Formula (i) wherein the metal is nickel is known from DE2327987 (1975).

The conversion of a compound of Compound (i) to the dye stabilizer of Formula 1 in reaction scheme III may be accomplished by a modified procedure of Suzuki (J. Am. Chem. Soc., 111, 314, 1989), according to which a fluorinating agent, such as perfluoroalkyl allyl ether, is first hydroborated with 9-borabicyclo[3.3.1]nonane in a solvent such as tetrahydrofuran or hexane. The crude organoborane complex thus obtained is then refluxed with the metal chelate bromide of Formula (i) in the presence of a catalyst, such as $PdCl_2(dppf)CH_2Cl_2$ and excess of aqueous NaOH.

Reaction scheme III is particularly favorable for the synthesis of a dye stabilizer of the present invention in which one of $R^1$–$R^5$ is $R_f$-A- wherein A is an alkylene.

II(D) Synthesis from 5-Bromosalicylic Acid for Formula 2

Reaction Scheme IV

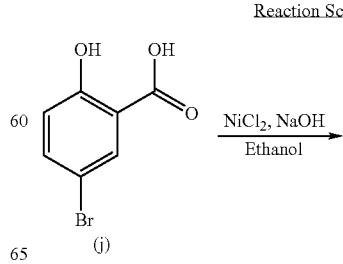

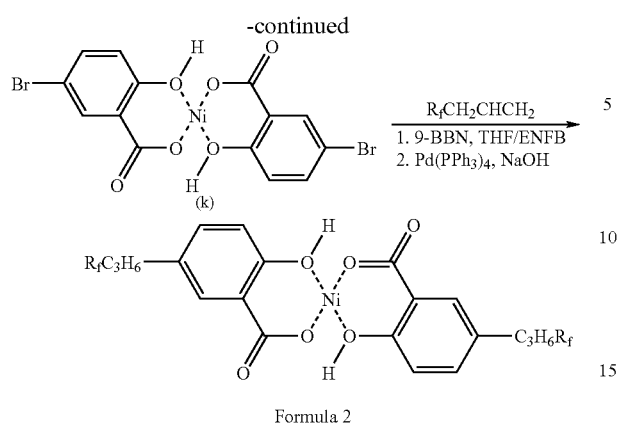

Formula 2

Reaction scheme IV illustrates the synthesis of the dye stabilizers of Formula 2 starting from 5-bromosalicylic acid (Compound j) which is commercially available (from, for example, Aldrich). The metal chelate of Formula (k) can be synthesized by refluxing an ethanolic solution of Compound (j) with a metal halide in a 2:1 ratio. The metal in the metal chelate of Formula (k) is nickel.

The conversion of Compound (k) to the dye stabilizer of Formula 2 in reaction scheme IV may be accomplished by a modified procedure of Suzuki in the same manner as the corresponding steps in reaction scheme III.

II(E) Synthesis from 5-Bromosalicylaldehyde for Formula 3

Reaction Scheme V

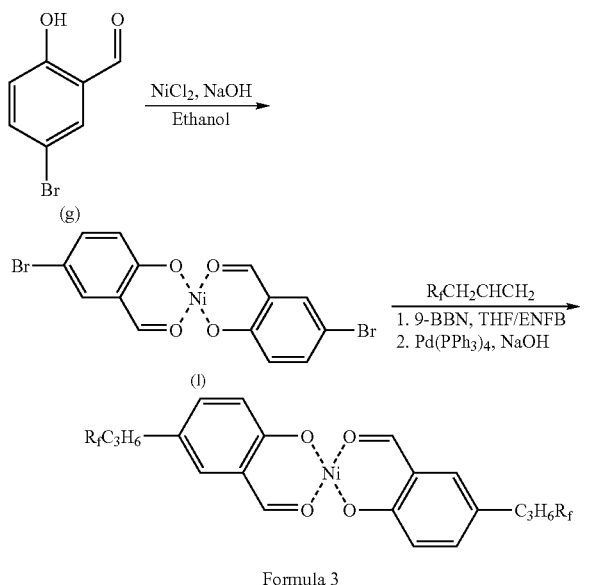

Formula 3

Reaction scheme V illustrates the synthesis of the dye stabilizers of Formula 3 starting from 5-bromosalicylaldehyde (Compound g) which is commercially available (from, for example, Aldrich). The metal chelate of Formula (l) can be synthesized by refluxing an ethanolic solution of Compound (g) with a metal halide in a 2:1 ratio.

The conversion of Compound (l) to the dye stabilizer of Formula 3 in reaction scheme V may be accomplished by a modified procedure of Suzuki in the same manner as the corresponding steps in reaction scheme III.

II(F) Synthesis from 2-Nitroaniline for Formula 4

Reaction Scheme VI

Reaction scheme VI illustrates the synthesis of the dye stabilizer or Formula 4 starting by diazotization of 2-nitroaniline (Compound m) which is commercially available (from, for example, Aldrich) and coupling of the resulting diazonium salt with a 4-bromophenol of Formula (n). The benzotriazole of Formula (p) can be synthesized by refluxing an ethanolic solution of Compound (o) with hydrazine hydrate in the presence of a Pd/Pt activated carbon catalyst.

The conversion of Compound (p) to the dye stabilizer of Formula 4 in reaction scheme VI may be accomplished by a modified procedure of Suzuki in the same manner as the corresponding steps in reaction scheme III.

II(G) Synthesis from 5-Bromo-2-hydroxybenzophenone for Formula 5

Reaction Scheme VII

-continued

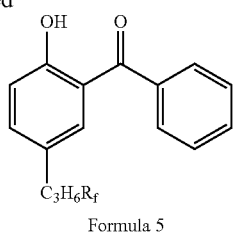

Formula 5

Reaction scheme VII illustrates the synthesis of the dye stabilizer of Formula 5 starting from 5-bromo-2-hydroxybenzophenone (Compound q) which is commercially available (from, for example, Aldrich). The synthesis may be accomplished by a modified procedure of Suzuki in the same manner as the corresponding steps in reaction scheme III.

II(H) Synthesis from 5-Bromosalicylic Acid for Formula 6

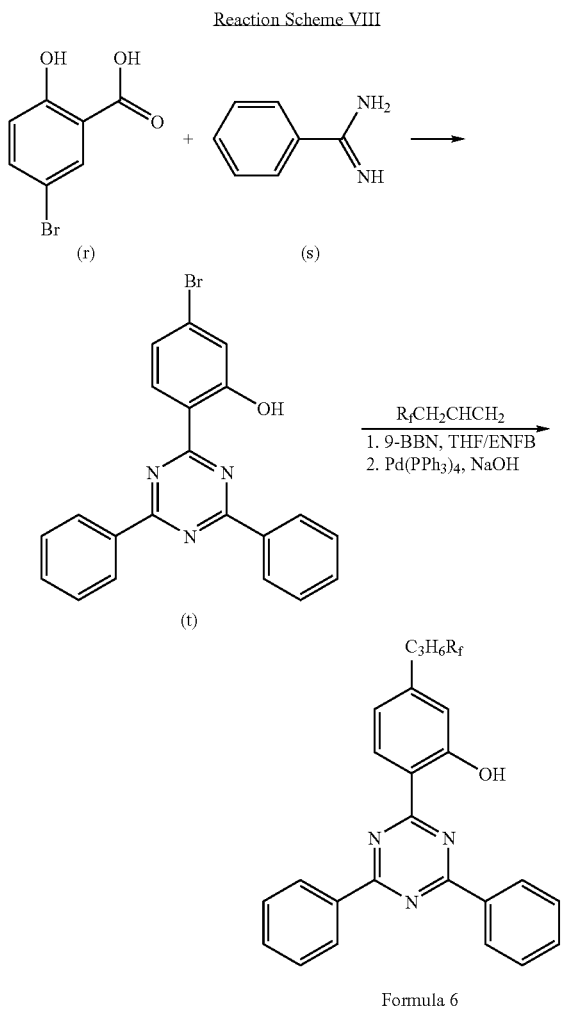

Formula 6

Reaction scheme VIII illustrates the synthesis of the dye stabilizer of Formula 6 starting from 5-bromosalicylic acid (Compound r) which is commercially available (from, for example, Aldrich) with a benzamidine of Formula (s). The conversion of Compound (t) to the dye stabilizer of Formula 6 in reaction scheme VIII may be accomplished by a modified procedure of Suzuki in the same manner as the corresponding steps in reaction scheme III.

The compounds of Formula 7 may be prepared by methods known in the art. For example, the 1,2-ethanedithiol nickel complex may be prepared by reacting $NiCl_2 \cdot 6H_2O$ with 1,2-ethanedithiol in the presence of 4,4-bipyzidine. More information on the synthesis of Formula 7 may be found in J. Phys. Chem., 1979, 83(5), 591–5 and J. Amer. Chem. Society., 1968, 90(5), 1139–1145.

III. Electrophoretic Fluid of the Invention

The electrophoretic fluid of the invention comprises charged pigment particles, a dye and a dye stabilizer of the invention.

The dye stabilizers of the present invention are highly soluble or dispersible in fluorinated solvents. While they are useful for stabilizing any types of dyes or colorants in a halogenated, in particular, fluorinated solvent, they are particularly effective in stabilizing halogenated, particularly fluorinated, dyes including silicon phthalocyanine or naphthalocyanine dyes as disclosed in the co-pending application, U.S. Ser. No. 10/439,428, filed on May 15, 2003, the content of which is incorporated herein by reference in its entirety.

Briefly, the fluorinated silicon phthalocyanine and naphthalocyanine dyes may be expressed by the following formulas:

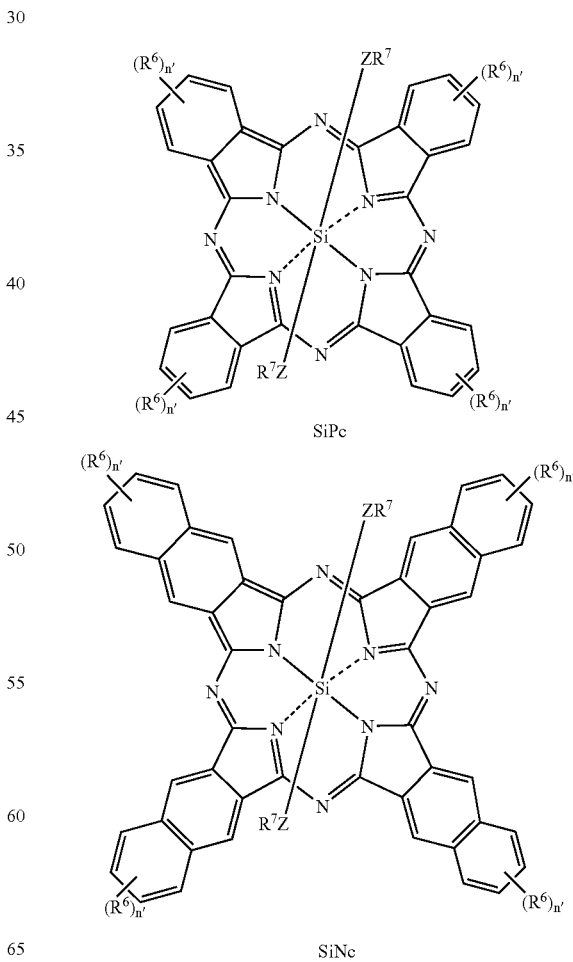

wherein:

n' is 0–4 for silicon phthalocyanine (SiPc) or 0–6 for silicon naphthalocyanine (SiNc);

$R^6$ is independently $R_f'$—X— (wherein $R_f'$ is as defined below and X is a single bond, —$CH_2O$—, —$CH_2CH_2$— or —CO—), alkyl, heteroalkyl, aryl, heteroaryl, alkylaryl, arylalkyl, heteroalkylaryl, alkyl-heteroaryl, heteroarylalkyl, aryl-heteroalkyl, R'O—, R'S—, R'R"N—, R'CO—, R'OCO—, R'COO—, R'CONR"—, R'R"NCO—, R'NHCONR"—, R'$SO_2$NR"—, R'R"$NSO_2$— or halogenated, particularly fluorinated, derivative thereof in which R' and R" are independently hydrogen, $R_f'$ (as defined below), alkyl, heteroalkyl, aryl, heteroaryl, alkylaryl, arylalkyl, heteroalkylaryl, alkyl-heteroaryl, heteroarylalkyl, aryl-heteroalkyl;

Z is O or NR' wherein R' is defined as above;

$R^7$ is hydrogen, $R_f'$—Y— (wherein $R_f'$ is as defined below and Y is a single bond, —$CH_2$— or —$CH_2CH_2$—), alkyl, heteroalkyl or halogenated, particularly fluorinated derivatives thereof, or —$SiR^8R^9R^{10}$ wherein $R^8$, $R^9$, and $R^{10}$ are independently an alkyl or fluoroalkyl group of 1 to 20 carbon atoms or alkoxy or fluoroalkoxy of 2 to 40 carbon atoms; and $R_f'$ is a fluorinated polymeric or oligomeric chain (M.W.=100–100,000).

It will be recognized that when the preparation of the compounds involves the reaction of a formed phthalocyanine/naphthalocyanine or silicon phthalocyanine/naphthalocyanine with a reagent that inserts $R^6$ groups, the resulting product may be a mixture of compounds having different degrees of $R^6$ substitution on the phthalocyanine/naphthalocyanine rings, so that n', when not 0, may be different on each of the phenyl or naphthyl moiety within a compound; and it will also be recognized that substitution may occur at different positions on the different phenyl/naphthyl rings of the phthalocyanine/naphthalocyanine; and all such compounds are suitable dyes for the present invention. In addition, when n' is not 0, not all $R^6$ groups need be the same, either within the compound as a whole or even on a particular phenyl or naphthyl moiety within a compound.

The substituents, $R^6$, $R^7$, $R^8$, $R^9$, $R^{10}$, $R_f'$ and n' of Formulas (SiPc) and (SiNc) are so selected that the total fluorine content of the silicon dye is at least 20%, preferably at least 30% and more preferably at least 50%, by weight of the dye molecule.

Synthesis of the silicon dyes of Formula (SiPc) and (SiNc) and preferred silicon dyes of Formula (SiPc) and (SiNc) are disclosed in the co-pending application, U.S. Ser. No. 10/439,428, filed on May 15, 2003, the content of which is incorporated herein by reference in its entirety.

The display fluid may be colored by one of the dyes of Formula (SiPc) or (SiNc) or a mixture thereof. The fluid may further comprise a second fluorinated metal phthalocyanine dye to enhance the color saturation. The metal may be Cu, Mg or Zn. These metal phthalocyanine dyes are available commercially or may be synthesized according to U.S. Pat. No. 3,281,426, the content of which is incorporated herein by reference in its entirety.

The preferred Cu phthalocyanine dyes are represented by Formula (CuPc) below:

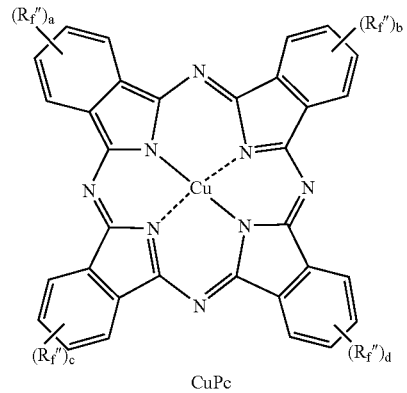

CuPc wherein $R_f''$ is $C_nH_xF_{2n+1-x}$ in which n is 1–18, preferably 4–12, x is 0–37, a, b, c and d are independently 0–4 provided that a+b+c+d≧3.

The use of a mixture of a dye of Formula SiPc or SiNc and a Cu phthalocyanine dye of Formula CuPc is preferable because the colorant mixture increases the low temperature (particularly subzero C) latitude of the display. This may be due to the higher solubility of the SiPc or SiNc dye in the electrophoretic fluid. By mixing a Si dye with a CuPc dye, a high contrast ratio can be achieved without the trade-off in the low temperature latitude. It also broadens the visible spectrum and increases the color saturation in a monochrome display. The ratio of the SiPc or SiNc dye to the CuPc dye in the mixture may range from 1/10 to 10/1, preferably 1/5 to 5/1 and more preferably 1/3 to 3/1.

The dye stabilizers of the present invention are highly soluble in fluorinated solvents particularly, perfluorinated solvents and have high extinction coefficients in the 500–700 nm region. A solvent having a low vapor pressure, a low viscosity and a dielectric constant in the range of about 1.5 to about 30, more preferably about 2 to about 10 are generally needed as the dielectric solvent of an electrophoretic fluid. Examples of suitable fluorinated solvents for EPD applications include, but are not limited to, perfluoro solvents such as perfluoroalkanes or perfluorocycloalkanes (e.g., perfluorodecalin), perfluoroarylalkanes (e.g., perfluorotoluene or perfluoroxylene), perfluoro-tert-amines, perfluoropolyethers such as those from Galden/Fomblin and perfluoropolyethers HT series, and hydrofluoropolyethers (ZT series) from Solvay Solexis, FC-43 (heptacosafluorotributylamine), FC-70 (perfluorotri-n-pentylamine), PF-5060 or PF-5060DL (perfluorohexane) from 3M Company (St. Paul, Minn.), low molecular weight (preferably less than 50,000, more preferably less than 20,000) polymers or oligomers such as poly(perfluoropropylene oxide) from TCI America (Portland, Oreg.), poly(chlorotrifluoroethylene) such as Halocarbon Oils from Halocarbon Product Corp. (River Edge, N.J.), Krytox® K-fluids (trifluorohomopolymer) from Dupont, and Demnum lubricating oils from Daikin Industries. In one embodiment, perfluoropolyethers and hydrofluoropolyethers such as Solvay Solexis HT-170, HT-200, HT-230, ZT-180 and Dupont trifluoro(trifluoromethyl)-oxirane homopolymers (such as K-6 and K-7 fluids) may be useful.

The charged pigment particles visually contrast with the fluorinated solvent in which the particles are suspended. The primary pigment particles may be organic or inorganic pigments, such as $TiO_2$, diarylide yellow, diarylide AAOT yellow, and quinacridone, azo, rhodamine, perylene pigment series from Sun Chemical, Hansa yellow G particles from Kanto Chemical and Carbon Lampblack from Fisher. The pigment particles may be prepared by any of the well-known methods including grinding, milling, attriting, microfluidizing and ultrasonic techniques. For example, pigment particles in the form of a fine powder are added to the suspending solvent and the resulting mixture is ball milled or attrited for several hours to break up the highly agglomerated dry pigment powder into primary particles. Particle size of the pigment particles is preferably in the range of about 0.01 to about 10 microns, more preferably in the range of about 0.05 to about 3 microns. These particles should have acceptable optical characteristics, should not be swollen or softened by the dielectric solvent and should be chemically stable. The resulting dispersion must also be stable against sedimentation, creaming or flocculation under normal operating conditions.

In order for the display composition to achieve high hiding power or light scattering efficiency, high dispersion stability, low rate of sedimentation or creaming and high mobility even with a high solid content and under a wide range of applied voltages, the pigment particles are preferably microencapsulated or coated with a polymer matrix of low specific gravity. Microencapsulation of the pigment particles may be accomplished chemically or physically. Typical microencapsulation processes include interfacial polymerization/crosslinking, in-situ polymerization/crosslinking, phase separation, simple or complex coacervation, electrostatic coating, spray drying, fluidized bed coating and solvent evaporation. Improved processes of making density-matched pigment microcapsules of high mobility involving the use of reactive protective colloids and charge controlling agents are disclosed in co-pending U.S. Ser. No. 10/335,210 filed on Dec. 31, 2002 (corresponding to WO 03/058335), U.S. Ser. No. 10/335,051 filed on Dec. 31, 2002 (corresponding to WO 03/057360) and U.S. Ser. No. 10/632,171 filed on Jul. 30, 2003, all of which are incorporated herein by reference in their entirety.

The dye stabilizer of the present invention is added into the electrophoretic fluid usually in the concentration of from 10 ppm to up to 5%, preferably from 50 ppm to up to 1%, more preferably from 100 ppm to 2000 ppm. The ratio of the dye stabilizer to the dye is preferably at least 1/1000, more preferably at least 3/1000.

The resulting display fluid may then be filled into the display cells and sealed.

IV. Electrophoretic Display of the Present Invention

The display cells may be the conventional partition type cells (as disclosed in M. A. Hopper and V. Novotny, IEEE Trans. Electr. Dev., Vol. ED 26, No. 8, pp. 1148–1152 (1979)), the microcapsule type cells (as disclosed in U.S. Pat. Nos. 5,961,804 and 5,930,026) and the display cells prepared from the microcup technology as disclosed in co-pending applications, U.S. Ser. No. 09/518,488, filed on Mar. 3, 2000 (corresponding to WO 01/67170 published on Sep. 13, 2001) the contents of all of which are incorporated herein by reference. The improved microcup-based display comprises isolated cells formed from microcups of well-defined shape, size and aspect ratio and filled with charged particles dispersed in a dielectric solvent or solvent mixture, preferably a halogenated solvent, particularly a perfluorinated solvent. The filled cells are individually sealed with a polymeric sealing layer, preferably formed from a composition comprising a material selected from a group consisting of thermoplastics, thermosets and precursors thereof.

EXAMPLES

Preparation 1

Synthesis of $R_f$-amine

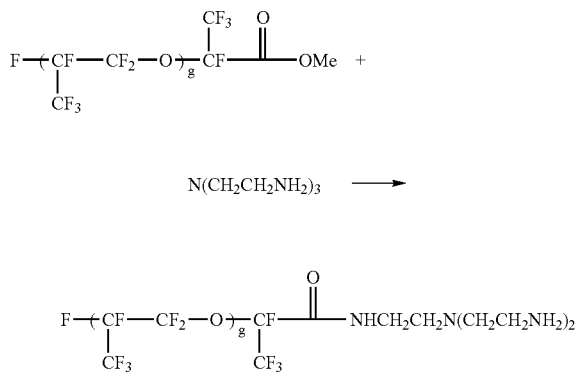

17.8 Grams of Krytox® methyl ester (DuPont, MW=about 1780, g=about 10) was dissolved in a solvent mixture containing 12 g of 1,1,2-trichlorotrifluoroethane (Aldrich) and 1.5 g of α,α,α-trifluorotoluene (Aldrich). The resultant solution was added drop by drop into a solution containing 7.3 g of tris(2-aminoethyl)amine (Aldrich) in 25 g of α,α,α-trifluorotoluene and 30 g of 1,1,2-trichlorotrifluoroethane over 2 hours with stirring at room temperature. The mixture was then stirred for another 8 hours to allow the reaction to complete. The IR spectrum of the crude product clearly indicated the disappearance of C=O vibration for methyl ester at 1780 $cm^{-1}$ and the appearance of C=O vibration for the amide product at 1695 $cm^{-1}$. Solvents were removed by rotary evaporation followed by vacuum stripping at 100° C. for 4–6 hours. The crude product was then dissolved in 50 mL of PFS2 solvent (perfluoropolyether from Solvay Solexis) and extracted with 20 mL of ethyl acetate three times, then dried to yield 17 g of purified product ($R_f$-amine1900) which showed excellent solubility in HT-200.

Other reactive $R_f$ amines having different molecular weights such as $R_f$-amine4900 (g=about 30), $R_f$-amine2000 (g=about 11), $R_f$-amine800 (g=about 4) and $R_f$-amine650 (g=about 3) may also be synthesized according to the same procedure.

Preparation 2
Synthesis of a Fluorinated Silicon Phthalocyanine
The Structure of SiPc-1:
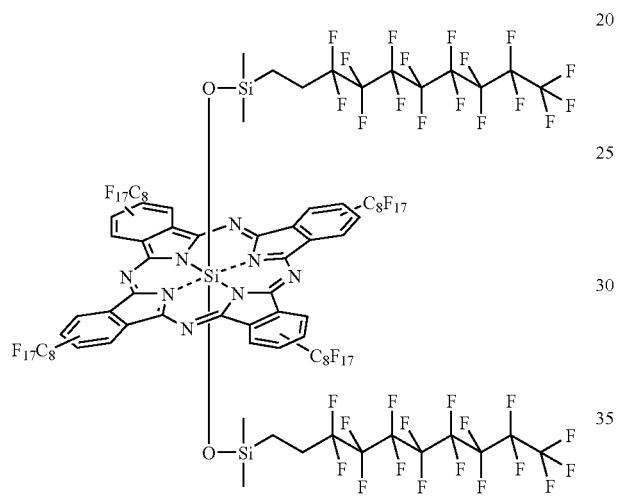

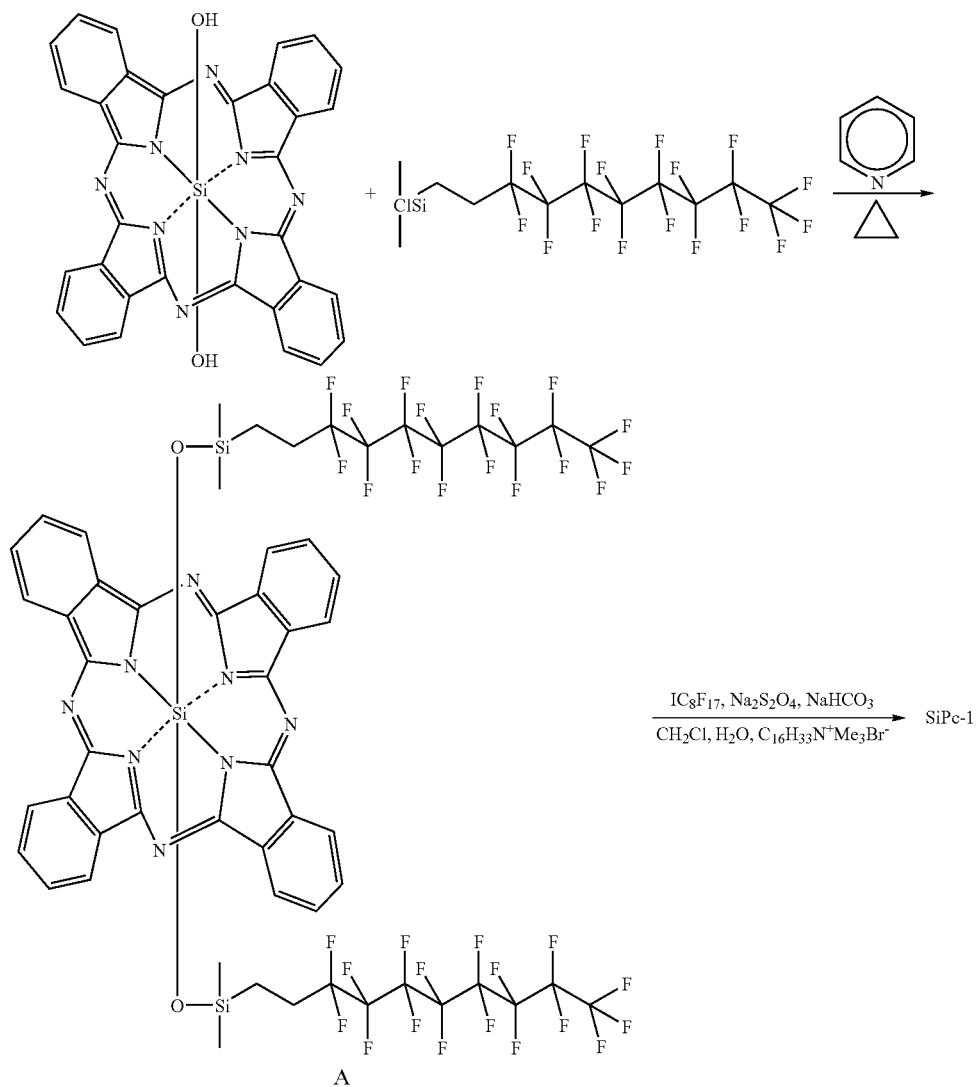

Scheme A: The synthetic route of SiPc-1

A. Synthesis of Compound A, SiPc(OSi(CH$_3$)$_2$(CH$_2$)$_2$(CF$_2$)$_7$ CF$_3$)$_2$ As shown in Scheme A, a mixture of (heptdecafluoro-1,1,2,2-tetrahydrodecyl)dimethylchlorosilane (2.50 g, 4.63 mmol, Gelest) and a suspension of SiPc(OH)$_2$ (1.00 g, 1.74 mmol, Aldrich) and pyridine (140 mL, Fisher Scientific), where each had been dried by distillation (~10 mL of distillate), was slowly distilled for 5 hours (~55 mL distillate). The resulting dark blue solution was evaporated to dryness by rotary evaporation (60° C.) under pump vacuum (1 Torr). The solid obtained was washed with an EtOH—H$_2$O mixture (1:1, 50 mL) and removed by filtration, dried (60° C., 60 Torr), dissolved in CH$_2$Cl$_2$ (120 mL) and filtered. The filtrate was evaporated to dryness by rotary evaporation (60° C.) under pump vacuum (1 Torr). A blue solid (2.26 g, 82% based on SiPc(OH)$_2$) was obtained.

B. The Synthesis of SiPc-1

A mixture of sodium dithionite (1.60 g, 9.19 mmol, Fluka) and sodium bicarbonate (0.80 g, 9.52 mmol, Aldrich) was added into a suspension containing the silicon phthalocyanine and SiPc(OSi(CH3)2(CH2)2(CF2)7CF3)2 (2.26 g, 1.43 mmol) obtained from Preparation 1A above. To the mixture, 1-iodoperfluorooctane (4.0 g, 7.33 mmol, Lancaster), cetyltrimethylammonium bromide (0.20 g, 0.55 mmol, Aldrich), CH$_2$Cl$_2$ (50 mL) and H$_2$O (50 mL) were added while being stirred vigorously at room temperature. The mixture obtained was kept stirring at room temperature for 18 hours, and then to which H$_2$O (20 mL) and PFS-2™ (40 mL) were added. The lower organic layer was separated and evaporated to dryness by rotary evaporation (60° C.) under pump vacuum (1 Torr). The dark blue oil obtained was chromatographed using PFS-2™ as the eluent through a column (1×10 cm) packed with $Al_2O_3$ III (neutral, Fisher Scientific). The fractions with the blue product were collected and evaporated to dryness by rotary evaporation (60° C.) under vacuum (~5 Torr). A blue solid, SiPc-1, was obtained (1.41 gm, 30% yield).

Preparation 3

Synthesis of a Fluorinated Cu Phthalocyanine Dye

The Structure of CuPc-1

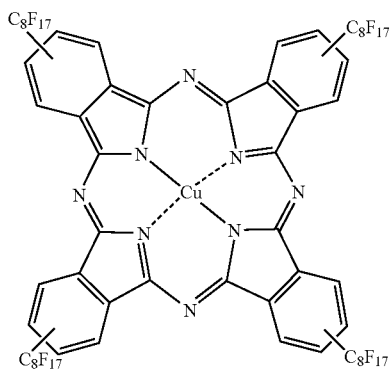

Scheme B: The synthetic route of CuPc-1

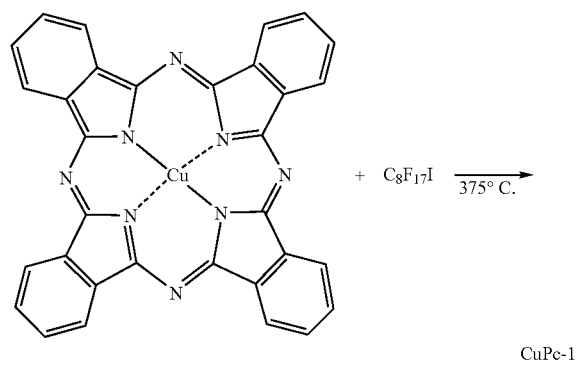

A fluorinated Cu phthalocyanine dye, CuPc-1, was prepared according to U.S. Pat. No. 3,281,426 (Scheme B). A mixture of copper phthalocyanine (41.0 g, 71.2 mmole, Aldrich) and 1-iodoperfluorooctane (370 g, 678 mmole, SynQuest) was added into a 1-gallon pressure reactor (Parr Instrument Co.) with a glass liner. The reactor was vacuum sealed at 1 Torr and heated at 375° C. for 3 days. The crude product obtained was mixed with 200 g of Celite (Fisher Scientific) and extracted with 4 L of PFS-2™ in Soxhlet extractor for 5 days. The dark blue solution obtained was washed with 4 L of acetone 3 times and evaporated to dryness by rotary evaporation (60° C.) under vacuum (~5 Torr). A dark blue solid, CuPc-1, was obtained (106 g, 66% yield).

Preparation 4

Synthesis of a Reactive Fluorinated Pyridinium Salt

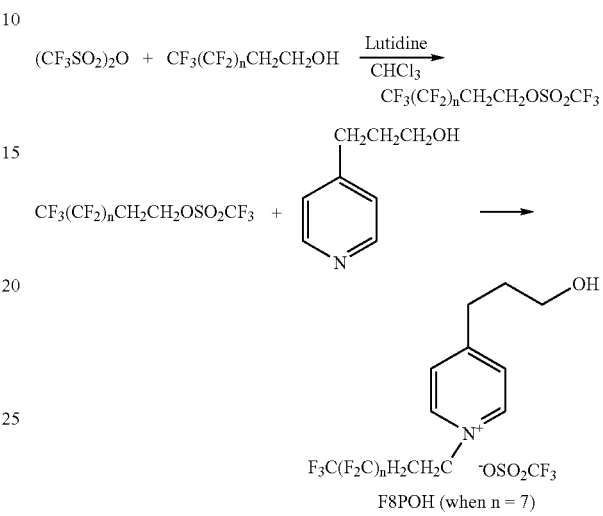

3.21 Grams (30.0 mmol) of 2,6-lutidine (Aldrich) and 11.6 g (25.0 mmol) of 1H, 1H, 2H, 2H-perfluorodecanol [$CF_3(CF_2)_nCH_2CH_2OH$, n=7] were dissolved in 150 mL of chloroform in a flask and cooled in a 0° C. bath. To the solution, 8.5 g (30.0 mmol) of trifluoromethanesulfonic anhydride pre-dissolved in 100 mL of chloroform was added drop-wise with stirring over a period of 30 minutes. The mixture was stirred for at least another 8 hours at room temperature to allow the reaction to complete. The reaction mixture was washed with deionized water three times, dried over magnesium sulfate and the solvent was stripped off. The crude product was recrystallized from heptane/methylene chloride and rinsed with heptane. 12.45 Grams (yield: 83.6%) of a white crystal (1H, 1H, 2H, 2H-perfluorodecyl triflate, $CF_3(CF_2)_nCH_2CH_2OSO_2CF_3$, n=7) was obtained.

5.96 Grams (10 mmol) of the thus obtained 1H, 1H, 2H, 2H-perfluorodecyl triflate was added into a solution containing 30 mL of methylene chloride and 1.37 g of (10 mmol) of 4-pyridinepropanol (Aldrich). The reaction mixture was stirred for 6 hours to allow the reaction to complete. After settling, the lower layer was separated and dried. 5.59 Grams of a light yellow solid, 1-(3,3,4,4,5,5,6,6,7,7,8,8,9,9, 10,10-heptadecafluoro-decyl)-4-(3-hydroxy-propyl)-pyridinium trifluoromethanesulfonate (hereinafter referred to as F8POH) was obtained.

Preparation 5

Preparation of $TiO_2$-Containing Microparticles 9.50 Grams of Desmodur® N3400 aliphatic polyisocyanate (from Bayer AG) and 0.49 g of TEA (triethanolamine from Dow) were dissolved in 3.79 g of acetone. To the resultant solution, 13 g of $TiO_2$ R706 (DuPont) was added and homogenized for 2 minutes 30 seconds with a rotor-stator homogenizer (IKA ULTRA-TURRAX T25) in room ambient; a solution containing 1.67 g of 1,5-pentanediol (BASF), 1.35 g of polypropylene oxide (MW=725 from Aldrich), 0.45 g of F8POH (from Preparation 4) and 2.47 g of acetone was added and homogenized for 1 minute. To the resultant solution, 0.32 g of an acetone solution containing 2% dibutyltin dilaurate (Aldrich) was added and homogenized for 2 minutes. Finally, 40.0 g of a HT-200 (Solvay Solexis) solution containing 0.8 g of $R_f$-amine4900, a precondensate of Krytox® methyl ester (DuPont, MW=about 4800) and tris(2-aminoethyl)amine (Aldrich) prepared according to Preparation 1, was added and homogenized for 2 minutes, following by addition of 33.0 g of a HT-200 solution containing 0.6 g of $R_f$-amine4900 and 0.35 gm of CuPc-1 (from Preparation 3) and homogenization for 2 minutes. The resultant microcapsule dispersion was then heated at 80° C. overnight and stirred under low shear to post cure the particles.

Example 1

Preparation of bis-2-Hydroxy-5-1'H,1'H,2'H,2'H-Perfluoro-1'-Decanoxyphenylketoxime Ni Chelate (Q1)

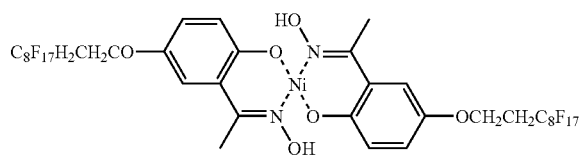

(Q1)

A. Synthesis of 2-hydroxy-5-1'H,1'H,2'H,2'H-perfluoro-1'-decanoxyacetophenone 0.76 Grams (5 mmole) of 2,5-dihydroxyacetophenone and 50 mL of acetone (which was dried over anhydrous potassium carbonate and distilled) were placed in a 250 mL round-bottomed flask fitted with a reflux condenser and a calcium guard tube. After the starting material was dissolved, 0.69 g (5 mmole) of anhydrous potassium carbonate was added followed by 2.96 g (5 mmole) of 1H,1H,2H,2H-perfluoro-1-decane triflate. The mixture was refluxed at 60–70° C. for about 24 hours. As much of the acetone as possible was removed by distillation. The residual dark-colored liquid was cooled and acidified with 10% HCl. The resulting mixture was extracted with 20 mL PFS-2 and washed with saturated saline (2×10 mL). The organic layer was separated, dried with $Na_2SO_4$ and concentrated. The residue was purified by flash column chromatography (10% EA/Hex) to yield 0.82 g (28%) of pale yellow solid. $^1$H NMR (400 MHz, $CDCl_3$): δ 11.90 (s, 1H, OH), 7.20 (d, 1H, ArH), 7.12 (dd, 1H, ArH), 6.95 (d, 1H, ArH), 4.25 (t, 2H, $OCH_2$), 2.62 (m, 2H, $CH_2$), 2.61 (s, 3H, $CH_3$). $^{19}$F NMR (400 MHz, $CDCl_3$): δ −80 (s, 3F, $CF_3$), −113 (s, 2F, $CF_2$), −121 (s, 6F, $CF_2$), −122 (s, 2F, $CF_2$), −123 (s, 2F, $CF_2$), −125 (s, 2F, $CF_2$).

B. Synthesis of 2-hydroxy-5-1'H,1'H,2'H,2'H-perfluoro-1'-decanoxyphenylketoxime 0.6 Grams (1 mmole) of the 2-hydroxy-5-1'H,1'H,2'H,2'H-perfluoro-1'-decanoxyacetophenone, 0.14 g (2 mmole) of hydroxylamine hydrochloride and 0.16 g (2 mmole) of pyridine were dissolved in 30 mL of methanol and refluxed for 10 hours. The solvent was evaporated and the remaining mixture was extracted with ether. The combined ether extract was washed with 10% HCl to remove the rest of pyridine and then with water (2×10 mL). The ether extract was dried with $Na_2SO_4$ and evaporated. A white solid of 0.6 g (98%) was obtained. $^1$H NMR (400 MHz, DMSO-$d_6$): δ 11.54 (s, 1H, NOH), 11.08 (s, 1H, OH), 7.01 (d, 1H, ArH), 6.89 (dd, 1H, ArH), 6.80 (d, 1H, ArH), 4.25 (t, 2H, $OCH_2$), 2.73 (m, 2H, $CH_2$), 2.24 (s, 3H, $CH_3$). $^{19}$F NMR (400 MHz, DMSO-$d_6$): δ −80 (s, 3F, $CF_3$), −112 (s, 2F, $CF_2$), −121 (s, 6F, $CF_2$), −122 (s, 2F, $CF_2$), −123 (s, 2F, $CF_2$), −125 (s, 2F, $CF_2$).

C. Synthesis of bis-2-hydroxy-5-1'H,1'H,2'H,2'H-perfluoro-1'-decanoxyphenylketoxime Ni chelate (Q1)

0.6 Grams (0.9 mmole) of 2-hydroxy-5-1'H,1'H,2'H,2'H-perfluoro-1'-decanoxyphenylketoxime and 0.04 g (1 mmole) of NaOH were stirred in 40 mL of ethanol. 0.06 Grams (0.46 mmole) of nickel chloride was added to the mixture and refluxed for 1 hour. After cooling and neutralizing with 10% HCl, the solid chelate was filtered off, washed copiously with water and dried at 60° C. A pale greenish solid of 0.46 g (74%) was obtained. $^1$H NMR (400 MHz, DMSO-$d_6$): δ 11.54 (s, 1H, NOH), 7.01 (d, 1H, ArH), 6.89 (dd, 1H, ArH), 6.80 (d, 1H, ArH), 4.25 (t, 2H, $OCH_2$), 2.72 (m, 2H, $CH_2$), 2.24 (s, 3H, $CH_3$). $^{19}$F NMR (400 MHz, DMSO-$d_6$): δ −80 (s, 3F, $CF_3$), −112 (s, 2F, $CF_2$), −121 (s, 6F, $CF_2$), −122 (s, 2F, $CF_2$), −123 (s, 2F, $CF_2$), −125 (s, 2F, $CF_2$).

Example 2

Preparation of bis-2-hydroxy-5-perfluorooctanylphenylketoxime Ni chelate (Q5)

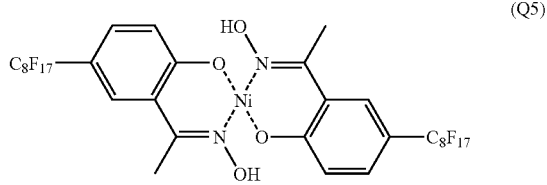

(Q5)

A. Synthesis of 2-hydroxy-5-perfluorooctanylacetophenone 1.36 Grams (10 mmole) of 2-hydroxyacetophenone was added to a solution of 0.4 g (10 mmole) NaOH in 10 mL water. To the resulting solution, a solution of 6.55 g (11.9 mmole) 1-iodoperfluorooctane in 25 mL of dimethylformamide was added and the mixture was stirred vigorously at room temperature. A solid mixture of 1.2 g (14.3 mmole) NaHCO$_3$ and 2.4 g (13.7 mmole) Na$_2$SO$_4$ was then added in small portions. The reaction was stirred at 40° C. for 24 hours, acidified with 10% HCl and extracted with ether (5(10 mL). The organic layer was washed with water (5(10 mL), dried with Na$_2$SO$_4$, and concentrated. The residue was purified by flash column chromatography (20% EA/Hex) to yield 0.55 g (10%) of a pale yellow solid. 1H NMR (400 MHz, DMSO-d6): (11.92 (s, 1H, OH), 7.84 (d, 1H, ArH), 7.50 (d, 1H, ArH), 7.09 (dd, 1H, ArH), 2.49 (s, 3H, CH3). 19F NMR (400 MHz, DMSO-d6): (−80 (s, 3F, CF3), −106 (s, 2F, CF2), −120 (s, 2F, CF2), −121 (s, 6F, CF2), −122 (s, 2F, CF2), −125 (s, 2F, CF2).

B. Synthesis of 2-hydroxy-5-perfluorooctanylpheylketoxime 0.55 Grams (0.9 mmole) of the 2-hydroxy-5-perfluorooctanylacetophenone, 0.13 g (1.8 mmole) of hydroxylamine hydrochloride and 0.15 g (1.8 mmole) of pyridine were dissolved in the 30 mL of methanol and refluxed for 10 hours. The solvent was evaporated and the remaining mixture was extracted with ether. The combined ether extract was washed with 10% HCl to remove the rest of pyridine and then with water (2×10 mL). The ether extract was dried with Na$_2$SO$_4$ and evaporated. A white solid of 0.54 g (96%) was obtained. $^1$H NMR (400 MHz, DMSO-d$_6$): δ 13.07 (s, 1H, NOH), 11.92 (s, 1H, OH), 7.84 (d, 1H, ArH), 7.50 (d, 1H, ArH), 7.09 (dd, 1H, ArH), 2.49 (s, 3H, CH$_3$). $^{19}$F NMR (400 MHz, DMSO-d$_6$): δ −80 (s, 3F, CF$_3$), −106 (s, 2F, CF$_2$), −120 (s, 2F, CF$_2$), −121 (s, 6F, CF$_2$), −122 (s, 2F, CF$_2$), −125 (s, 2F, CF$_2$).

C. Synthesis of bis-2-hydroxy-5-perfluorooctanylphenylketoxime Ni chelate (Q5)

0.5 Grams (0.87 mmole) of 2-hydroxy-5-perfluorooctanylpheylketoxime and 0.04 g (1 mmole) of NaOH were stirred in the 40 mL of ethanol. 0.06 Grams (0.46 mmole) of nickel chloride was added to the mixture and refluxed for 1 hour. After cooling and neutralizing with 10% HCl, the solid chelate was filtered off, washed copiously with water and dried at 60° C. A pale greenish solid of 0.17 g (32%) was obtained. $^1$H NMR (400 MHz, A113): δ 10.14 (s, 1H, NOH), 7.48 (d, 1H, ArH), 7.26 (d, 1H, ArH), 6.63 (dd, 1H, ArH), 2.43 (s, 3H, CH$_3$). $^{19}$F NMR (400 MHz, A113): δ −82 (s, 3F, CF$_3$), −109 (s, 2F, CF$_2$), −121 (s, 2F, CF$_2$), −122 (s, 6F, CF$_2$), −123 (s, 2F, CF$_2$), −126 (s, 2F, CF$_2$).

Example 3

Preparation of bis-2-hydroxy-5-krytoxphenylaldoxime Ni chelate (Q7)

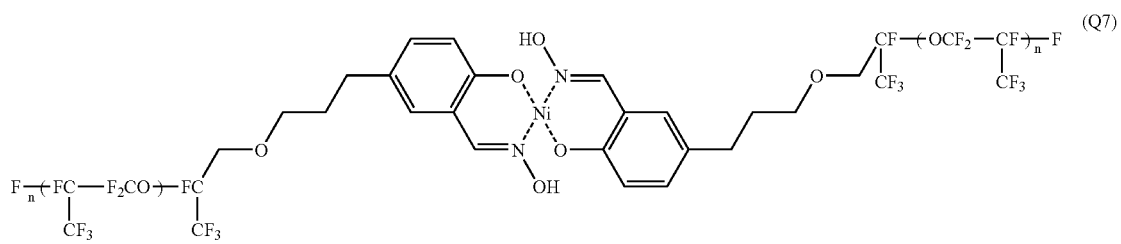

(Q7)

A. Synthesis of 2-hydroxy-5-bromopheylaldoxime 6.0 Grams (29.8 mmole) of the 5-bromosalicylaldehyde, 4.15 g (59.7 mmole) of hydroxylamine hydrochloride and 5.20 g (65.8 mmole) of pyridine were dissolved in the 50 mL of methanol and refluxed for 10 hours. The solvent was evaporated and the remaining mixture was extracted with ether. The combined ether extract was washed with 10% HCl to remove the rest of pyridine and then washed with water (2×10 mL). The ether extract was dried with Na$_2$SO$_4$ and evaporated. A white solid of 6.0 g (93%) was obtained. $^1$H NMR (400 MHz, CDCl$_3$): δ 9.86 (s, 1H, CHN), 8.15 (s, 1H, OH), 8.07 (s, 1H, NOH), 7.36 (dd, 1H, ArH), 7.28 (d, 1H, ArH), 6.87 (d, 1H, ArH).

B. Synthesis of bis-2-hydroxy-5-bromopheylaldoxime Ni chelate 6.6 Grams (30 mmole) of 2-hydroxy-5-bromopheylaldoxime and 1.22 g (30 mmole) of NaOH were stirred in the 50 mL of ethanol. 1.95 Grams (15 mmole) of nickel chloride was added to the mixture and refluxed for 1 hour. After cooling and neutralizing with 10% HCl, the solid chelate was filtered off, washed copiously with water and dried at 60° C. A greenish solid of 4.19 g (56%) was obtained. 1H NMR (400 MHz, CDCl3): (9.86 (s, 1H, CHN), 8.07 (s, 1H, NOH), 7.36 (dd, 1H, ArH), 7.28 (d, 1H, ArH), 6.87 (d, 1H, ArH).

C. Synthesis of bis-2-hydroxy-5-krytoxphevlaldoxime Ni chelate (Q7)

A solution of 25 mL (11.25 mmole) 9-borabicyclo[3.3.1] nonane in 0.45–0.50 M of tetrahydrofuran was added drop-wise to a stirring solution of 4 g (2.2 mmole) Krytox allyl ether (MW=1750) and ethyl perfluorobutyl ether 10 mL at 0° C. The resulting suspension was stirred as room temperature for 24 hours, during which time the mixture became homogeneous. 15 Milliliters of 3M of aqueous NaOH was added to the mixture and the mixture was stirred for 30 minutes. The solution was transferred into the mixture of 0.56 g (1.1 mmole) bis-2-hydroxy-5-bromopheylaldoxime Ni chelate and 0.23 g (0.19 mmole) Pd(PPh3)4 under Ar and refluxed for 24 hours. The resulting mixture was extracted with 20 mL perfluoropolyether PFS-2 (Solvay Solexis) and washed with water (2×10 mL) and acetone (5×10 mL). The organic layer was separated, dried with $Na_2SO_4$, and concentrated. The residue was purified by flash column chromatography (10% ether/PFS-2) to yield 2.33 g (53%) of a greenish oil. 1H NMR (400 MHz, A113): 10.49 (s, 1H, CHN), 7.74 (s, 1H, NOH), 6.96 (dd, 1H, ArH), 6.84 (d, 1H, ArH), 6.68 (d, 1H, ArH), 3.99 (s, 2H, CH2), 3.54 (s, 2H, CH2), 2.62 (s, 2H, CH2), 1.87 (s, 2H, CH2). 19F NMR (400 MHz, A113): (−80, −82, −130, and −145).

Examples 4–7

Photochemical Stability of SiPc-1 dye with a Dye Stabilizer

An HT-200 solution containing 40 ppm of SiPc-1 from Preparation 2 and 0 or 100 ppm of a dye stabilizer was placed in a cuvette (optical path=1 cm), wrapped with a PET film (from DuPont, 5 mil), covered with a pyrex glass slide and exposed with either (1) a high intensity UV lamp (Fusion D lamp, 2 W/cm2) or (2) a collimated 150 W Xe—Arc lamp at a distance of 10 cm. The UV spectra were measured and the % degradation of the absorbance of SiPc-1 at 620 nm was recorded.

The effect of the stabilizers Q5 and Q7 on photochemical stability of the SiPc-1 dye in HT-200 (a perfluoropolyether solvent from Solvay Solexis) is summarized in Table 1.

TABLE 1

Effect of Q5 and Q7 on the photostability of SiPc-1

| Example | Dye | Stabilizer | % degradation after 1 hr of irradiation(1, 2) | % degradation after 2 hrs of irradiation(1, 2) |
|---|---|---|---|---|
| 4 (Comparative) | SiPc-1 | None | 18%[1] | — |
| 5 | SiPc-1 | 100 ppm of Q5 | 11%[1] | 17%[1] |
| 6 (Comparative) | SiPc-1 | None | — | 11%[2] |
| 7 | SiPc-1 | 100 ppm of Q7 | — | 0%[2] |

[1]Exposed with a Fusion D lamp (2 W/cm$^2$)
[2]Exposed with a 150 W Xe-Arc lamp.

It is evident from Table 1 that both stabilizers, Q5 and Q7, significantly improve the photostability of SiPc-1.

Examples 8–9

Effects of Dye Stabilizers on Photostability of the EPD Contrast Ratio

An electrophoretic fluid containing 9.7 wt % (dry weight) of the $TiO_2$-containing particles from Preparation 5, 0.8 wt % of CuPc-1 from Preparation 3, 0.4 wt % of SiPc-1 from Preparation 2 and 0 or 100 ppm of stabilizer Q7 from Example 3 was prepared. The electrophoretic fluid was injected into an EPD cell having a cell gap of 35 μm between two ITO/PET films which were precoated with a thin (about 3 μm) layer of polyurethane P9820 (from Huntsman Polyurethanes). The filled EPD cells were then sealed with Norland 65 UV adhesive.

The samples were switched to their Dmax state and exposed for 17 hours to a high intensity visible light transmitted from an optical fiber equipped with a standard EKE bulb with its IR radiation filtered-off by D.I. water (2.5 cm thick in the optical path) in a glass vial. The results are summarized in Table 2.

TABLE 2

Effect of Q7 on the Photostability of EPD Contrast Ratio

| Example | Concentration (ppm of Q7 in EPD fluid | Exposure (hrs) | Dmin | Contrast Ratio[1] |
|---|---|---|---|---|
| 8 | 100 | 0 | 0.79 | 7.1 |
|   | 100 | 17 | 0.77 | 7.6 |
| 9 (Comparative) | 0 | 0 | 0.76 | 7.4 |
|   | 0 | 17 | 1.624 | 1.1 |

[1]Driving conditions: +/−40 V, 0.2 Hz.

It can be seen that EPDs containing 100 ppm of stabilizer Q7 in the electrophoretic fluid (Example 8) showed essentially no change in contrast ratio and Dmin. In contrast, EPDs without the stabilizer Q7 (Comparative Example 9) showed dramatic changes both in contrast ratio and Dmin.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, materials, compositions, processes, process step or steps, to the objective, spirit and scope of the present invention. All such modifications are intended to be within the scope of the claims appended hereto.

It is therefore wished that this invention to be defined by the scope of the appended claims as broadly as the prior art will permit, and in view of the specification.

What is claimed is:

1. A dye stabilizer represented by the following formula:

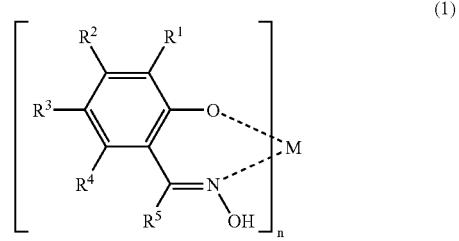

wherein:
M is a metal ion;
n is 2 or 3;
$R^1$, $R^2$, $R^3$, $R^4$ and $R^5$ are, independently, $R_f$-A- (wherein $R_f$ and A are defined below), hydrogen, hydroxyl, halogen, nitro, cyano, alkyl, heteroalkyl, aryl, heteroaryl, alkylaryl, arylalkyl, alkyl-heteroaryl, heteroalkylaryl, aryl-heteroalkyl, heteroarylalkyl, alkoxy, aryloxy, benzoyl, acetyl, carbonyl, sulfonyl, amido, carbamoyl, sulfonamido, sulfamoyl or heterocyclyl, or any two of $R^1$, $R^2$, $R^3$, $R^4$ or $R^5$ together form a cycloalkyl or heterocyclic group, provided that at least one of $R^1$, $R^2$, $R^3$, $R^4$ and $R^5$ is $R_f$-A-;

A in $R_f$-A- is absent, oxygen or an alkylene chain; and $R_f$ is a fluorinated alkyl, a fluorinated aryl, or a fluorinated polymeric or oligomeric moiety.

2. The dye stabilizer of claim 1 wherein said metal ion is a divalent metal ion.

3. The dye stabilizer of claim 2 wherein said metal ion is Co, Cu, Fe, Mn, Ni, Zr, Pd, Pt or Zn ion.

4. The dye stabilizer of claim 3 wherein said metal ion is Ni ion.

5. The dye stabilizer of claim 1 wherein $R_f$ is prepared from one or more types of fluorinated monomers selected from the group consisting of epoxide, hydrofuran, cyclolactone, cyclolactam, acrylate, methacrylate and vinyl.

6. The dye stabilizer of claim 1 wherein $R_f$ is:

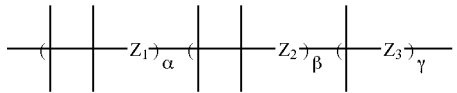

wherein the open and not designated substituent positions on the main chain of $R_f$ are independently selected from the group consisting of hydrogen, halogen, alkyl, aryl, alkylaryl, fluoroalkyl, fluoroaryl, fluoroalkylaryl, —$OR^{11}$, $OCOR^{11}$, —$COOR^{11}$, —$CONR^{11}R^{12}$ (wherein $R^{11}$ and $R^{12}$ are independently hydrogen, alkyl, aryl, alkylaryl, fluoroalkyl, fluoroaryl, fluoroalkylaryl or fluorinated polyether) and substituted derivatives thereof;

$Z_1$, $Z_2$, and $Z_3$ are independently oxygen or absent;

α, β and γ are the weight fractions of the corresponding repeating units and are independently in the range of 0–1 with their sum no greater than 1.

7. The dye stabilizer of claim 1 wherein one of $R^1$, $R^2$, $R^3$, $R^4$ and $R^5$ is $R_f$-A- and the remaining four are independently hydrogen or alkyl.

8. The dye stabilizer of claim 7 wherein one of $R^1$, $R^2$, $R^3$ and $R^4$ is $R_f$-A-, $R^5$ is alkyl and the remaining three are all hydrogen.

9. The dye stabilizer of claim 8 wherein $R^5$ is methyl.

10. The dye stabilizer of claim 7 wherein A in $R_f$-A- is oxygen or absent and $R_f$ is a completely or partially fluorinated alkyl of 6 to 20 carbon atoms.

11. The dye stabilizer of claim 6 wherein A in $R_f$-A- is oxygen or an alkylene chain and $R_f$ is a fluorinated polymeric or oligomeric chain.

12. The dye stabilizer of claim 11 wherein $R_f$ is:

wherein the open and not designated substituent positions on the main chain of $R_f$ are independently selected from the group consisting of hydrogen, halogen, alkyl, aryl, alkylaryl, fluoroalkyl, fluoroaryl, fluoroalkylaryl, —$OR^{11}$, $OCOR^{11}$, —$COOR^{11}$, —$CONR^{11}R^{12}$ (wherein $R^{11}$ and $R^{12}$ are independently hydrogen, alkyl, aryl, alkylaryl, fluoroalkyl, fluoroaryl, fluoroalkylaryl or fluorinated polyether) and substituted derivatives thereof;

$Z_1$, $Z_2$, and $Z_3$ are independently oxygen or absent;

α, β and γ are the weight fractions of the corresponding repeating units and are independently in the range of 0–1 with their sum no greater than 1.

13. The dye stabilizer of claim 12 wherein the open substituent positions are independently hydrogen, fluorine or fluorinated alkyl.

14. The dye stabilizer of claim 11 wherein said fluorinated polymeric or oligomeric chain is a fluorinated polyether.

15. A dye stabilizer represented by Formula 2 or 3:

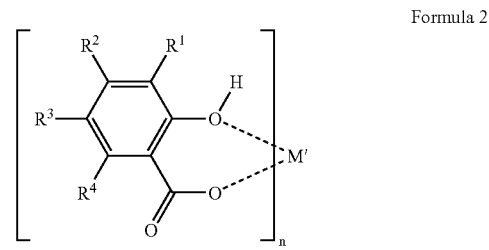

Formula 2

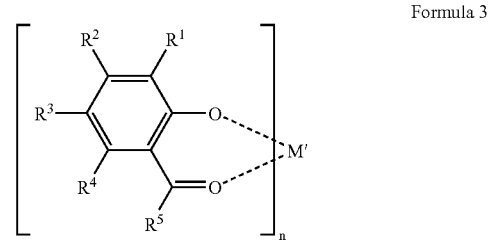

Formula 3 wherein:

M' is absent or a metal ion;

n is 2 or 3;

$R^1$, $R^2$, $R^3$, $R^4$ and $R^5$ are independently, $R_f$-A- (wherein $R_f$ and A are defined below), hydrogen, hydroxyl, halogen, nitro, cyano, alkyl, heteroalkyl, aryl, heteroaryl, alkylaryl, arylalkyl, alkyl-heteroaryl, heteroalkylaryl, aryl-heteroalkyl, heteroarylalkyl, alkoxy, aryloxy, benzoyl, acetyl, carbonyl, sulfonyl, amido, carbamoyl, sulfonamido, sulfamoyl or heterocyclyl, or any two of $R^1$, $R^2$, $R^3$ or $R^4$ in Formula 2 or any two of $R^1$, $R^2$, $R^3$, $R^4$ or $R^5$ in Formula 3 together form a cycloalkyl or heterocyclic group, provided that at least one of $R^1$, $R^2$, $R^3$ and $R^4$ Formula 2 and at least one of $R^1$, $R^2$, $R^3$, $R^4$ and $R^5$ in Formula 3 is $R_f$-A-;

A in $R_f$-A- is absent, oxygen or an alkylene chain; and $R_f$ is a fluorinated alkyl, or a fluorinated aryl, or a fluorinated polymeric or oligomeric moiety.

16. The dye stabilizer of claim 15 wherein said metal ion is Ni, Go, Cu, Fe, Mn, Zr, Pd, Pt, Mg, Al or Zn.

17. The dye stabilizer of claim 15 wherein $R_f$ is prepared from one or more types of fluorinated monomers selected from the group consisting of epoxide, hydrofuran, cyclolactone, cyclolactam, acrylate, methacrylate and vinyl.

18. A dye stabilizer represented by Formula 4, 5 or 6:

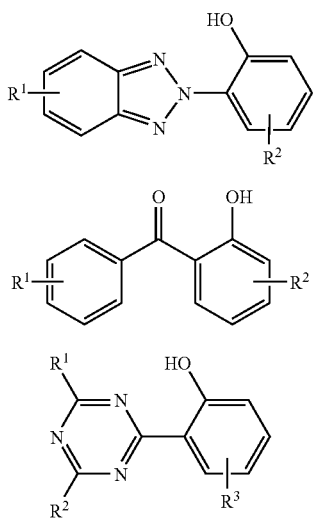

wherein:
$R^1$, $R^2$ and $R^3$ are independently, $R_f$-A- (wherein $R_f$ and A are defined below), hydrogen, hydroxyl, halogen, nitro, cyano, alkyl, heteroalkyl, aryl, heteroaryl, alkylaryl, arylalkyl, alkyl-heteroaryl, heteroalkylaryl, aryl-heteroalkyl, heteroarylalkyl, alkoxy, aryloxy, benzoyl, acetyl, carbonyl, sulfonyl, amido, carbamoyl, sulfonamido, sulfamoyl or heterocyclyl, provided at least one of $R^1$ and $R^2$ in Formula 4 or 5 and at least one of $R^1$, $R^2$ and $R^3$ in Formula 6 is $R_f$-A-;

A in $R_f$-A- is absent, oxygen or an alkylene chain; and $R_f$ is a fluorinated alkyl, a fluorinated aryl, or a fluorinated polymeric or oligomeric moiety.

19. The dye stabilizer of claim 18 wherein $R_f$ is prepared from one or more types of fluorinated monomers selected from the group consisting of epoxide, hydrofuran, cyclolactone, cyclolactam, acrylate, methacrylate and vinyl.

20. A dye stabilizer represented by the formula 7:

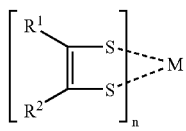

wherein:
M is a metal ion;
N is 2 or 3;
one of $R^1$ and $R^2$ is $R_f$-A-, the other is hydrogen or alkyl;
A in $R_f$-A- is absent, oxygen or an alkylene chain; and
$R_f$ is a fluorinated alkyl, a fluorinated aryl, or a fluorinated polymeric or oligomeric moiety.

21. The dye stabilizer of claim 20 wherein said metal ion is Co, Cu, Fe, Mn, Ni, Zr, Pd, Pt or Zn ion.

22. The dye stabilizer of claim 1, 15, 18 or 20 wherein A in $R_f$-A- is absent and $R_f$ is a completely or partially fluorinated alkyl of 6–20 carbon atoms.

23. The dye stabilizer of claim 1, 15, 18 or 20 wherein $R^1$, $R^2$, $R^3$, $R^4$ and $R^5$ in Formulas 1 and 3, $R^1$, $R^2$, $R^3$ and $R^4$ in Formula 2, $R^1$ and $R^2$ in Formulas 4, 5 and 7 and $R^1$, $R^2$ and $R^3$ in Formula 6 are so selected that the total fluorine content of the dye stabilizer molecule is at least 10% by weight of the molecule.

24. The dye stabilizer of claim 23 wherein the total fluorine content of the dye stabilizer molecule is at least 20% by weight of the molecule.

25. The dye stabilizer of claim 24 wherein the total fluorine content of the dye stabilizer molecule is at least 50% by weight of the molecule.

26. An electrophoretic fluid comprising charged pigment particles dispersed in a dieletric solvent or solvent mixture, a dye or dye mixture and a dye stabilizer represented by Formula 1:

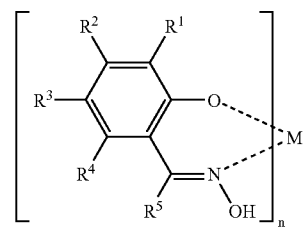

(1)

M is a metal ion;
n is 2 or 3;
$R^1$, $R^2$, $R^3$, $R^4$ and $R^5$ are, independently, $R_f$-A- (wherein $R_f$ and A are defined below), hydrogen, hydroxyl, halogen, nitro, cyano, alkyl, heteroalkyl, aryl, heteroaryl, alkylaryl, arylalkyl, alkyl-heteroaryl, heteroalkylaryl, aryl-heteroalkyl, heteroarylalkyl, alkoxy, aryloxy, benzoyl, acetyl, carbonyl, sulfonyl, amido, carbamoyl, sulfonamido, sulfamoyl or heterocyclyl, or any two of $R^1$, $R^2$, $R^3$, $R^4$ or $R^5$ together form a cycloalkyl or heterocyclic group, provided that at least one of $R^1$, $R^2$, $R^3$, $R^4$ and $R^5$ is $R_f$-A-;

A in $R_f$-A- is absent, oxygen or an alkylene chain; and $R_f$ is a fluorinated alkyl, a fluorinated aryl, or a fluorinated polymeric or oligomeric moiety.

27. The electrophoretic fluid of claim 26 wherein said metal ion is Co, Cu, Fe, Mn, Ni, Zr, Pd, Pt or Zn ion.

28. The electrophoretic fluid of claim 27 wherein said metal ion is Ni ion.

29. The electrophoretic fluid of claim 26 wherein $R_f$ is prepared from one or more types of fluorinated monomers selected from the group consisting of epoxide, hydrofuran, cyclolactone, cyclolactam, acrylate, methacrylate and vinyl.

30. The electrophoretic fluid of claim 26 wherein one of $R^1$, $R^2$, $R^3$, $R^4$ and $R^5$ is $R_f$-A- and the remaining four are independently hydrogen or alkyl.

31. The electrophoretic fluid of claim 30 wherein one of $R^1$, $R^2$, $R^3$ and $R^4$ is $R_f$-A-, $R^5$ is alkyl and the remaining three are all hydrogen.

32. The electrophoretic fluid of claim 31 wherein $R^5$ is methyl.

33. The electrophoretic fluid of claim 30 wherein A in $R_f$-A- is oxygen or absent and $R_f$ is a completely or partially fluorinated alkyl of 6 to 20 carbon atoms.

34. The electrophoretic fluid of claim 30 wherein A in $R_f$-A- is oxygen or an alkylene chain and $R_f$ is a fluorinated polymeric or oligomeric chain.

35. The electrophoretic fluid of claim 34 wherein $R_f$ is:

wherein the open and not designated substituent positions on the main chain of $R_f$ are independently selected from the group consisting of hydrogen, halogen, alkyl, aryl, alkylaryl, fluoroalkyl, fluoroaryl, fluoroalkylaryl, —OR$^{11}$, OCOR$^{11}$, —COOR$^{11}$, —CONR$^{11}$R$^{12}$ (wherein R$^{11}$ and R$^{12}$ are independently hydrogen, alkyl, aryl, alkylaryl, fluoroalkyl, fluoroaryl, fluoroalkylaryl or fluorinated polyether) and substituted derivatives thereof;

$Z_1$, $Z_2$, and $Z_3$ are independently oxygen or absent;

$\alpha$, $\beta$ and $\gamma$ are the weight fractions of the corresponding repeating units and are independently in the range of 0–1 with their sum no greater than 1.

36. The electrophoretic fluid of claim 35 wherein the open substituent positions are independently hydrogen, fluorine or fluorinated alkyl.

37. The electrophoretic fluid of claim 34 wherein said fluorinated polymeric or oligomeric chain is a fluorinated polyether.

38. The electrophoretic fluid of claim 30 wherein A in $R_f$-A- is absent and $R_f$ is a completely or partially fluorinated alkyl of 6–20 carbon atoms.

39. The electrophoretic fluid of claim 26 wherein said dye is a Si phthalocyanine or napthalocyanine dye.

40. The electrophoretic fluid of claim 39 wherein said Si phthalocyanine or napthalocyanine dye is represented by the following formula SiPc or SiNc:

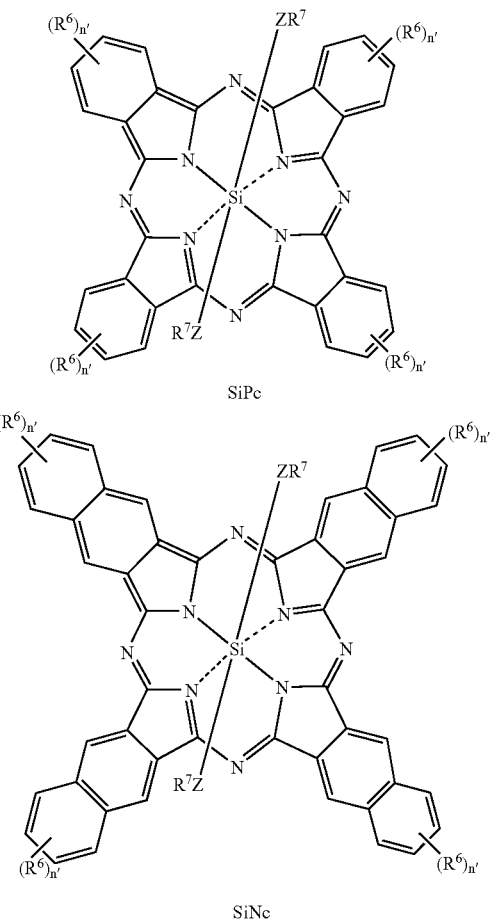

wherein:

n' is 0–4 for silicon phthalocyanine or 0–6 for silicon naphthalocyanine;

R$^6$ is independently $R_f'$—X— (wherein $R_f'$ is as defined below and X is a single bond, —CH$_2$O—, —CH$_2$CH$_2$O— or —CO—), alkyl, heteroalkyl, aryl, heteroaryl, alkylaryl, arylalkyl, heteroalkylaryl, alkylheteroaryl, heteroarylalkyl, aryl-heteroalkyl, R'O—, R'S—, R'R"N—, R'CO—, R'OCO—, R'COO—, R'CONR"—, R'R"NCO—, R'NHCONR"—, R'SO$_2$NR"—, R'R"NSO$_2$— or halogenated, particularly fluorinated, derivative thereof in which R' and R" are independently hydrogen, $R_f'$ (as defined below), alkyl, heteroalkyl, aryl, heteroaryl, alkylaryl, arylalkyl, heteroalkylaryl, alkyl-heteroaryl, heteroarylalkyl, arylheteroalkyl;

Z is O or NR' wherein R' is defined as above;

R$^7$ is hydrogen, $R_f'$—Y— (wherein $R_f'$ is as defined below and Y is a single bond, —CH$_2$— or —CH$_2$CH$_2$—), alkyl, heteroalkyl or halogenated, particularly fluorinated derivatives thereof, or —SiR$^8$R$^9$R$^{10}$ wherein R$^8$, R$^9$, and R$^{10}$ are independently an alkyl or fluoroalkyl group of 1 to 20 carbon atoms or alkoxy or fluoroalkoxy of 2 to 40 carbon atoms; and $R_f'$ is a fluorinated polymeric or oligomeric chain having molecular weight between 100–100,000.

41. The electrophoretic fluid of claim 40 wherein the substituents, R$^6$, R$^7$, R$^8$, R$^9$, R$^{10}$, $R_f'$, and n' are so selected that the total fluorine content of the silicon phthalocyanine dye is at least 20% by weight of the dye molecule.

42. The electrophoretic fluid of claim 41 wherein the substituents, R$^6$, R$^7$, R$^8$, R$^9$, R$^{10}$, $R_f'$, and n' are so selected that the total fluorine content of the silicon phthalocyanine dye is at least 30% by weight of the dye molecule.

43. The electrophoretic fluid of claim 42 wherein the substituents, R$^6$, R$^7$, R$^8$, R$^9$, R$^{10}$, $R_f'$, and n' are so selected that the total fluorine content of the silicon phthalocyanine dye is at least 50% by weight of the dye molecule.

44. The electrophoretic display of claim 26 wherein said dye mixture comprises a Si phthalocyanine or naphthalocyanine dye and a Cu phthalocyanine dye.

45. The electrophoretic display of claim 44 wherein said Cu phthalocyanine dye is represented by the following formula:

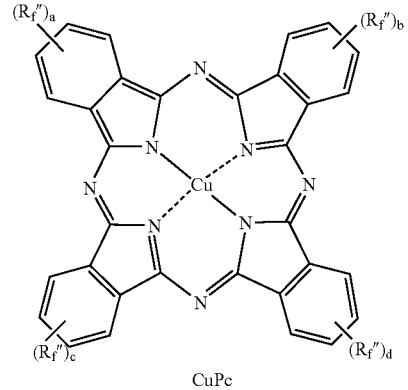

wherein $R_f''$ is $C_nH_xF_{2n+1-x}$ in which n is 1–18, x is 0–37, a, b, c and d are independently 0–4 provided that a+b+c+d≧3.

46. The electrophoretic fluid of claim 45 wherein n is 4–12.

47. The electrophoretic fluid of claim 44 wherein the ratio of the Si phthalocyanine or naphthalocyanine dye to the Cu phthalocyanine dye is 1/10 to 10/1.

48. The electrophoretic fluid of claim 47 wherein the ratio of the Si phthalocyanine or naphthalocyanine dye to the Cu phthalocyanine dye is 1/5 to 5/1.

49. The electrophoretic fluid of claim 48 wherein the ratio of the Si phthalocyanine or naphthalocyanine dye to the Cu phthalocyanine dye is 1/3 to 3/1.

50. The electrophoretic fluid of claim 26 wherein said dielectric solvent is a halogenated solvent.

51. The electrophoretic fluid of claim 50 wherein said solvent is a fluorinated solvent.

52. The electrophoretic fluid of claim 51 wherein said fluorinated solvent is selected from the group consisting of perfluoroalkanes, perfluorocycloalkanes, perfluoroarylalkanes, perfluoro-tert-amines, perfluoropolyethers, hydrofluoropolyethers and poly(chlorotrifluoroethylene).

53. The electrophoretic fluid of claim 52 wherein said perfluoropolyether and hydrofluoropolyether are selected from the group consisting of Solvay Solexis HT-170, HT-200, HT-230, ZT-180 and Dupont trifluoro(trifluoromethyl)-oxirane homopolymers K-6 and K-7 fluids.

54. An electrophoretic display comprising display cells filled with an electrophoretic fluid which comprises charged pigment particles dispersed in a dielectric solvent or solvent mixture, a dye or dye mixture and a dye stabilizer represented by the following formula:

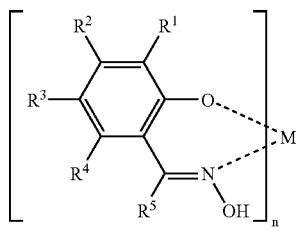

(1)

wherein:

M is a metal ion;

n is 2 or 3;

$R^1$, $R^2$, $R^3$, $R^4$ and $R^5$ are, independently, $R_f$-A- (wherein $R_f$ and A are defined below), hydrogen, hydroxyl, halogen, nitro, cyano, alkyl, heteroalkyl, aryl, heteroaryl, alkylaryl, arylalkyl, alkyl-heteroaryl, heteroalkylaryl, aryl-heteroalkyl, heteroarylalkyl, alkoxy, aryloxy, benzoyl, acetyl, carbonyl, sulfonyl, amido, carbamoyl, sulfonamido, sulfamoyl or heterocyclyl, or any two of $R^1$, $R^2$, $R^3$, $R^4$ or $R^5$ together form a cycloalkyl or heterocyclic group, provided that at least one of $R^1$, $R^2$, $R^3$, $R^4$ and $R^5$ is $R_f$-A-;

A in $R_f$-A- is absent, oxygen or an alkylene chain; and $R_f$ is a fluorinated alkyl or aryl or a low/medium molecular weight fluorinated polymeric or oligomeric moiety.

55. The display of claim 54, wherein said display cells are microcups.

56. The display of claim 54 which is prepared by a microencapsulation process.

57. An electrophoretic fluid comprising charged pigment particles dispersed in a dieletric solvent or solvent mixture, a dye or dye mixture and a dye stabilizer of claim 15, 18 or 20.

58. An electrophoretic display comprising display cells filled with an electrophoretic fluid which comprises charged pigment particles dispersed in a dielectric solvent or solvent mixture, a dye or dye mixture and a dye stabilizer of claim 15, 18 or 20.

59. The dye stabilizer of claim 6 wherein said halogen is a fluorine.

60. The dye stabilizer of claim 12 wherein said halogen is a fluorine.

61. The dye stabilizer of claim 35 wherein said halogen is a fluorine.

62. The dye stabilizer of claim 1, wherein $R_f$ has a molecular weight of about 100 to about 100,000.

* * * * *